US011518804B2

(12) United States Patent
MacDonald et al.

(10) Patent No.: US 11,518,804 B2
(45) Date of Patent: *Dec. 6, 2022

(54) METHOD OF TREATING OSTEOARTHRITIS WITH AN ANTIBODY TO NGF

(71) Applicant: REGENERON PHARMACEUTICALS, INC., Tarrytown, NY (US)

(72) Inventors: Lynn MacDonald, Harrison, NY (US); Richard Torres, New York, NY (US); Marc R. Morra, Beacon Falls, CT (US); Joel H. Martin, Putnam Valley, NY (US); Joel C. Reinhardt, Mount Kisco, NY (US); Paul Tiseo, Greenwich, CT (US)

(73) Assignee: REGENERON PHARMACEUTICALS, INC., Tarrytown, NY (US)

( * ) Notice: Subject to any disclaimer, the term of this patent is extended or adjusted under 35 U.S.C. 154(b) by 230 days.

This patent is subject to a terminal disclaimer.

(21) Appl. No.: 16/926,232

(22) Filed: Jul. 10, 2020

(65) Prior Publication Data

US 2020/0339672 A1    Oct. 29, 2020

Related U.S. Application Data

(63) Continuation of application No. 16/282,120, filed on Feb. 21, 2019, now Pat. No. 10,745,471, which is a continuation of application No. 15/144,574, filed on May 2, 2016, now Pat. No. 10,266,588, which is a continuation of application No. 14/038,349, filed on Sep. 26, 2013, now Pat. No. 9,353,176, which is a continuation of application No. 13/648,477, filed on Oct. 10, 2012, now Pat. No. 8,637,031, which is a continuation of application No. 12/888,751, filed on Sep. 23, 2010, now Pat. No. 8,309,088, which is a continuation-in-part of application No. 12/188,330, filed on Aug. 8, 2008, now Pat. No. 7,988,967.

(60) Provisional application No. 61/246,261, filed on Sep. 28, 2009, provisional application No. 61/079,259, filed on Jul. 9, 2008, provisional application No. 61/062,860, filed on Jan. 28, 2008, provisional application No. 60/994,526, filed on Sep. 20, 2007, provisional application No. 60/964,224, filed on Aug. 10, 2007.

(51) Int. Cl.
| | | |
|---|---|---|
| C07K 16/22 | (2006.01) |
| A61K 39/395 | (2006.01) |
| A61K 45/06 | (2006.01) |
| A61K 9/00 | (2006.01) |
| A61K 39/00 | (2006.01) |

(52) U.S. Cl.
CPC ............ *C07K 16/22* (2013.01); *A61K 9/0019* (2013.01); *A61K 39/3955* (2013.01); *A61K 45/06* (2013.01); *A61K 2039/505* (2013.01); *A61K 2039/545* (2013.01); *C07K 2317/51* (2013.01); *C07K 2317/515* (2013.01); *C07K 2317/56* (2013.01); *C07K 2317/565* (2013.01); *C07K 2317/76* (2013.01)

(58) Field of Classification Search
CPC ................ C07K 16/22; C07K 2317/51; C07K 2317/515; C07K 2317/56; C07K 2317/565; C07K 2317/76; A61K 9/0019; A61K 39/3955; A61K 2039/505; A61K 2039/545; A61K 45/06; A61P 29/00; A61M 5/20; A61M 5/2033; A61M 2005/206; A61M 2005/2073; A61M 5/24; A61M 5/178

See application file for complete search history.

(56) References Cited

U.S. PATENT DOCUMENTS

| | | |
|---|---|---|
| 5,147,294 A | 9/1992 | Smith et al. |
| 6,548,062 B2 | 4/2003 | Buchkovich et al. |
| 7,252,822 B2 | 8/2007 | Shelton et al. |
| 7,255,860 B2 | 8/2007 | Shelton et al. |
| 7,425,329 B2 | 9/2008 | Shelton et al. |
| 7,449,616 B2 | 11/2008 | Pons et al. |
| 7,569,364 B2 | 8/2009 | Rosenthal et al. |
| 7,601,352 B1 | 10/2009 | Novak et al. |
| 7,601,818 B2 | 10/2009 | Wild et al. |
| 7,655,231 B2 | 2/2010 | Shelton et al. |
| 7,655,232 B2 | 2/2010 | Pons et al. |
| 7,727,527 B2 | 6/2010 | Shelton |

(Continued)

FOREIGN PATENT DOCUMENTS

| | | |
|---|---|---|
| WO | WO 2002/096458 | 12/2002 |
| WO | WO 2004/016769 | 2/2004 |

(Continued)

OTHER PUBLICATIONS

Casset, F. et al., "A peptide mimetic of an anti-CD4 monoclonal antibody by rational design" Biochem Biophys Res Commun. (2003) 307(1 ):198-205.

Chen et al., "Selection and analysis of an optimized anti-VEGF antibody: crystal structure of an affinity-matured Fab in complex with antigen" J. Mol. Biol. (1999) 293(4):865-881.

Foote et al., "Antibody Framework Residues Affecting the Conformation of the Hypervariable Loops" J. Molec. Biol. (1992) 224(2):487-499.

(Continued)

*Primary Examiner* — Kimberly Ballard
(74) *Attorney, Agent, or Firm* — Karl Bozicevic; Bozicevic, Field & Francis LLP

(57) ABSTRACT

Methods are disclosed for treating osteoarthritis in a human subject in need thereof, comprising administering to the subject a therapeutically effective amount of an anti-human NGF antibody, or antigen-binding fragment thereof, wherein at least one symptom associated with osteoarthritis is prevented, ameliorated or improved.

28 Claims, 1 Drawing Sheet

Specification includes a Sequence Listing.

(56) References Cited

U.S. PATENT DOCUMENTS

| | | |
|---|---|---|
| 7,795,413 B2 | 9/2010 | Wild, Jr. et al. |
| 2004/0071701 A1 | 4/2004 | Delafoy et al. |
| 2004/0131615 A1 | 7/2004 | Shelton et al. |
| 2004/0237124 A1 | 11/2004 | Pons et al. |
| 2007/0253930 A1 | 11/2007 | Roy et al. |
| 2008/0107658 A1 | 5/2008 | Franks et al. |
| 2009/0041717 A1 | 2/2009 | Macdonald et al. |
| 2009/0208490 A1 | 8/2009 | Pavone et al. |
| 2009/0300780 A1 | 12/2009 | Cattaneo et al. |
| 2010/0278839 A1 | 11/2010 | Powell et al. |

FOREIGN PATENT DOCUMENTS

| | | | |
|---|---|---|---|
| WO | WO 2004/058184 | 7/2004 | |
| WO | WO-2004096122 A2 * | 11/2004 | ........... A61K 31/485 |
| WO | WO 2005/019266 | 3/2005 | |
| WO | WO 2005/056601 | 6/2005 | |
| WO | WO 2006/110883 | 10/2006 | |
| WO | WO 2006/131951 | 12/2006 | |
| WO | WO 2006/131952 | 12/2006 | |
| WO | WO 2007/024846 | 5/2007 | |
| WO | WO-2008005315 A2 * | 1/2008 | ........... A61M 5/2033 |

OTHER PUBLICATIONS

Holm, P. et al., "Functional mapping and single chain construction of the anti-cytokeratin 8 monoclonal antibody TS1" Mol. Immunol. (2007) 44(6):1075-1084.

Jackowski et al., "Neural injury repair: hope for the future as barriers to effective CNS regeneration become clearer" British Journal of Neurosurgery, (1995) 9:303-317.

Maccallum et al., "Antibody-antigen interactions: contact analysis and binding site topography" J. Mol. Biol. (1996) 262:732-745.

Padlan et al., "Structure of an antibody-antigen complex: crystal structure of the HyHEL-10 Fab-lysozyme complex" Proc. Natl. Acad. Sci. USA (1989) 86:5938-5942.

Rudikoff et al., "Single amino acid substitution altering antigen-binding specificity" Proc. Natl. Acad. Sci USA (Mar. 1982) 79(6):1979-1983.

Safieh-Garabedian, B., et al., "Contribution of interleukin-1 beta to the inflammation-induced increase in nerve growth factor levels and inflammatory hyperalgesia" Brit. J. Pharmacol. (1995) 115:1265-1275.

Vajdos, FF et al., "Comprehensive functional maps of the antigen-binding site of an anti-ErbB2 antibody obtained with shotgun scanning mutagenesis" J. Mol. Biol. (2002) 320(2):415-428.

We, P. Fundamental Immunology, Third Edition, Raven Press, New York (1993) pp. 292-295.

Wilson-Gerwing et al., "Neurotrophin-3 suppresses thermal hyperalgesia associated with neuropathic pain and attenuates transient receptor potential vanilloid receptor-1 expression in adult sensory neurons" J. Neuroscience (2005) 25(3):758-767.

Winter et al., "Humanized Antibodies" Immunology Today (1993) 14(6):243-246.

* cited by examiner

Study Flowchart

| Study Procedure | Visit 1 | Treatment and Observation Period ||||||||||
|---|---|---|---|---|---|---|---|---|---|---|---|
| | | Visit 2 | Visit 3 | Visit 4 | Visit 5 | Visit 6 | Visit 7 | Visit 8 | Visit 9 | Visit 10 | End-of-Study |
| Day(s) | -14 to -3 | 1 | 8 | 15 | 29 | 57 | 71 | 85 | 113 | 141 | 169 |
| Randomization | | X | | | | | | | | | |
| Administration of Study Drug | | X | | | | X | | | | | |
| Inclusion/Exclusion | X | | | | | | | | | | |
| Informed Consent | X | | | | | | | | | | |
| Medical History | X | | | | | | | | | | |
| Demographics | X | | | | | | | | | | |
| X-ray of affected knee | | | | | | | | | | | |
| Physical Examination | X | | | | | X | | | | | X |
| Vital Signs | X | X | X | X | X | X | X | X | X | X | X |
| Weight | X | | | | | X | | | | | X |
| Height | X | | | | | | | | | | |
| Electrocardiogram | X | | | | | X | | | | | X |
| Serum pregnancy | X | | | | | | | | | | |
| Urine pregnancy | | X | | | | X | | | | | X |
| Hematology Panel | X | X | | | X | X | | X | X | X | X |
| Chemistry Panel | X | X | | | X | X | | X | X | X | X |
| Urinalysis | X | X | | | X | X | | X | X | X | X |
| Adverse Events | X | X | X | X | X | X | X | X | X | X | X |
| Concomitant Medications | X | X | X | X | X | X | X | X | X | X | X |
| Neurological Evaluation | | X | X | X | X | X | X | X | X | X | X |
| Walking Knee Pain | | X | X | X | X | X | X | X | X | X | X |
| WOMAC | | X | X | X | X | X | X | X | X | X | X |
| Patient Global Impression of Change | | | X | | X | X | | X | X | X | X |
| SF-12 QOL Questionnaire | | X | | | X | X | | X | X | X | X |
| PK Blood Sample | | X | X | X | X | X | X | X | X | X | X |
| Anti-R475 Ab blood sample | | X | | | | X | | X | | | X |
| Exploratory Proteomic Sample | | X | X | | X | X | | X | | | X |
| Exploratory RNA Sample | | X | X | | X | X | | X | | | X |

SEQUENCE LISTING

<160> NUMBER OF SEQ ID NOS: 59

<210> SEQ ID NO 1
<211> LENGTH: 847
<212> TYPE: DNA
<213> ORGANISM: Homo sapiens

<400> SEQUENCE: 1

| | | |
|---|---|---|
| agcgtccgga cccaataaca gttttaccaa gggagcagct ttctatcctg gccacactga | 60 |
| ggtgcatagc gtaatgtcca tgttgttcta cactctgatc acagcttttc tgatcggcat | 120 |
| acaggcggaa ccacactcag agagcaatgt ccctgcagga cacaccatcc cccaagccca | 180 |
| ctggactaaa cttcagcatt cccttgacac tgcccttcgc agagcccgca gcgcccggc | 240 |
| agcggcgata gctgcacgcg tggcggggca gacccgcaac attactgtgg accccaggct | 300 |
| gttaaaaag cggcgactcc gttcaccccg tgtgctgttt agcacccagc ctccccgtga | 360 |
| agctgcagac actcaggatc tggacttcga ggtcggtggt gctgccccct caacaggac | 420 |
| tcacaggagc aagcggtcat catcccatcc catcttccac aggggcgaat tctcggtgtg | 480 |
| tgacagtgtc agcgtgtggg ttggggataa gaccaccgcc acagacatca agggcaagga | 540 |
| ggtgatggtg ttgggagagg tgagcattaa caacagtgta ttcaaacagt actttttga | 600 |
| gaccaagtgc cgggacccaa atcccgttga cagcgggtgc cggggcattg actcaaagca | 660 |
| ctggaactca tattgtacca cgactcacac ctttgtcaag gcgctgacca tggatggcaa | 720 |
| gcaggctgcc tggcggttta tccggataga tacggcctgt atgtgtgtgc tcagcaggaa | 780 |
| ggctgtgaga agagcctgac ctgccgacac gctccctccc cctgccctt ctacactctc | 840 |
| ctgggcc | 847 |

<210> SEQ ID NO 2
<211> LENGTH: 115
<212> TYPE: PRT
<213> ORGANISM: Homo sapiens

<400> SEQUENCE: 2

Ser Ser Ser His Pro Ile Phe His Arg Gly Glu Phe Ser Val Val Ser
1               5                  10                  15

Val Trp Val Gly Asp Lys Thr Thr Ala Thr Asp Ile Lys Gly Lys Glu
            20                  25                  30

Val Met Val Leu Gly Glu Val Asn Ile Asn Asn Ser Val Phe Lys Gln
        35                  40                  45

Tyr Phe Phe Glu Thr Lys Cys Arg Asp Pro Asn Pro Val Asp Ser Gly
    50                  55                  60

Cys Arg Gly Ile Asp Ser Lys His Trp Asn Ser Tyr Cys Thr Thr Thr
65                  70                  75                  80

His Thr Phe Ala Leu Thr Met Asp Gly Lys Gln Ala Ala Trp Arg Phe
                85                  90                  95

Ile Arg Ile Asp Thr Ala Cys Val Cys Val Leu Ser Arg Lys Ala Val
            100                 105                 110

Arg Arg Ala
        115

<210> SEQ ID NO 3
<211> LENGTH: 357
<212> TYPE: DNA
<213> ORGANISM: Artificial Sequence
<220> FEATURE:
<223> OTHER INFORMATION: Synthetic

<400> SEQUENCE: 3

```
caggtgcagc tggtacagtc tggggctgag gtgaagaagc ctggggcctc agtgaaggtc    60
tcctgcaagg tttccggatt caccctcact gaattatcca ttcactgggt gcgacaggct   120
cctgaaaaag gcttgagtg gatgggaggt tttgatcctg aagatggtga acaatctac    180
gcacagaagt tccagggcag agtcaccatg accgaggaca catctacaga cacagcctac   240
atggagctga ccagcctgag atcggaagac acggccgtgt attactgttc aacgattttt   300
ggagtggtta ccaactttga caactggggc cagggaaccc tggtcaccgt ctcctca     357
```

<210> SEQ ID NO 4
<211> LENGTH: 119
<212> TYPE: PRT
<213> ORGANISM: Artificial Sequence
<220> FEATURE:
<223> OTHER INFORMATION: Synthetic

<400> SEQUENCE: 4

```
Gln Val Gln Leu Val Gln Ser Gly Ala Glu Val Lys Lys Pro Gly Ala
  1               5                  10                  15
Ser Val Lys Val Ser Cys Lys Val Ser Gly Phe Thr Leu Thr Glu Leu
                 20                  25                  30
Ser Ile His Trp Val Arg Gln Ala Pro Gly Lys Gly Leu Glu Trp Met
             35                  40                  45
Gly Gly Phe Asp Pro Glu Asp Gly Glu Thr Ile Tyr Ala Gln Lys Phe
         50                  55                  60
Gln Gly Arg Val Thr Met Thr Glu Asp Thr Ser Thr Asp Thr Ala Tyr
 65                  70                  75                  80
Met Glu Leu Thr Ser Leu Arg Ser Glu Asp Thr Ala Val Tyr Tyr Cys
                 85                  90                  95
Ser Thr Ile Phe Gly Val Val Thr Asn Phe Asp Asn Trp Gly Gln Gly
            100                 105                 110
Thr Leu Val Thr Val Ser Ser
        115
```

<210> SEQ ID NO 5
<211> LENGTH: 24
<212> TYPE: DNA
<213> ORGANISM: Artificial Sequence
<220> FEATURE:
<223> OTHER INFORMATION: Synthetic

<400> SEQUENCE: 5

```
ggattcaccc tcactgaatt atcc                                            24
```

<210> SEQ ID NO 6
<211> LENGTH: 8
<212> TYPE: PRT
<213> ORGANISM: Artificial Sequence
<220> FEATURE:
<223> OTHER INFORMATION: Synthetic

<400> SEQUENCE: 6

```
Gly Phe Thr Leu Thr Glu Leu Ser
  1               5
```

<210> SEQ ID NO 7
<211> LENGTH: 24
<212> TYPE: DNA
<213> ORGANISM: Artificial Sequence

```
<220> FEATURE:
<223> OTHER INFORMATION: Synthetic

<400> SEQUENCE: 7
tttgatcctg aagatggtga aaca                                          24

<210> SEQ ID NO 8
<211> LENGTH: 8
<212> TYPE: PRT
<213> ORGANISM: Artificial Sequence
<220> FEATURE:
<223> OTHER INFORMATION: Synthetic

<400> SEQUENCE: 8

Phe Asp Pro Glu Asp Gly Glu Thr
 1               5

<210> SEQ ID NO 9
<211> LENGTH: 36
<212> TYPE: DNA
<213> ORGANISM: Artificial Sequence
<220> FEATURE:
<223> OTHER INFORMATION: Synthetic

<400> SEQUENCE: 9
tcaacgattt ttggagtggt taccaacttt gacaac                             36

<210> SEQ ID NO 10
<211> LENGTH: 12
<212> TYPE: PRT
<213> ORGANISM: Artificial Sequence
<220> FEATURE:
<223> OTHER INFORMATION: Synthetic

<400> SEQUENCE: 10

Ser Thr Ile Phe Gly Val Val Thr Asn Phe Asp Asn
 1               5                  10

<210> SEQ ID NO 11
<211> LENGTH: 324
<212> TYPE: DNA
<213> ORGANISM: Artificial Sequence
<220> FEATURE:
<223> OTHER INFORMATION: Synthetic

<400> SEQUENCE: 11
gacatccgga tgacccagtc tccatcctcc ctgtctgcat ctgcaggaga cagagtcacc    60
atcacttgcc gggcaagtca ggccattaga aatgatttag ctggtatca  gcagaaacca   120 gggaaagccc ctaagcgcct gatctatgct gcattcaatt tgcaaagtgg ggtcccatca   180
agattcagcg gcagtggatc tgggacagaa ttcactctca caatcagtag cctgcagcct   240
gaagatcttg caagttatta ctgtcaacag tataatagat acccgtggac gttcggccaa   300
gggaccaagc tggagatcaa acga                                         324

<210> SEQ ID NO 12
<211> LENGTH: 107
<212> TYPE: PRT
<213> ORGANISM: Artificial Sequence
<220> FEATURE:
<223> OTHER INFORMATION: Synthetic

<400> SEQUENCE: 12

Asp Ile Arg Met Thr Gln Ser Pro Ser Ser Leu Ser Ala Ser Ala Gly
 1               5                  10                  15
```

```
Asp Arg Val Thr Ile Thr Cys Arg Ala Ser Gln Ala Ile Arg Asn Asp
            20                  25                  30

Leu Gly Trp Tyr Gln Gln Lys Pro Gly Lys Ala Pro Lys Arg Leu Ile
        35                  40                  45

Tyr Ala Ala Phe Asn Leu Gln Ser Gly Val Pro Ser Arg Phe Ser Gly
50                  55                  60

Ser Gly Ser Gly Thr Glu Phe Thr Leu Thr Ile Ser Ser Leu Gln Pro
65                  70                  75                  80

Glu Asp Leu Ala Ser Tyr Tyr Cys Gln Gln Tyr Asn Arg Tyr Pro Trp
                85                  90                  95

Thr Phe Gly Gln Gly Thr Lys Leu Glu Ile Lys
            100                 105

<210> SEQ ID NO 13
<211> LENGTH: 18
<212> TYPE: DNA
<213> ORGANISM: Artificial Sequence
<220> FEATURE:
<223> OTHER INFORMATION: Synthetic

<400> SEQUENCE: 13
caggccatta gaaatgat                                                     18

<210> SEQ ID NO 14
<211> LENGTH: 6
<212> TYPE: PRT
<213> ORGANISM: Artificial Sequence
<220> FEATURE:
<223> OTHER INFORMATION: Synthetic

<400> SEQUENCE: 14

Gln Ala Ile Arg Asn Asp
1               5

<210> SEQ ID NO 15
<211> LENGTH: 9
<212> TYPE: DNA
<213> ORGANISM: Artificial Sequence
<220> FEATURE:
<223> OTHER INFORMATION: Synthetic

<400> SEQUENCE: 15 gctgcattc                                                                9

<210> SEQ ID NO 16
<211> LENGTH: 3
<212> TYPE: PRT
<213> ORGANISM: Artificial Sequence
<220> FEATURE:
<223> OTHER INFORMATION: Synthetic

<400> SEQUENCE: 16

Ala Ala Phe
1

<210> SEQ ID NO 17
<211> LENGTH: 27
<212> TYPE: DNA
<213> ORGANISM: Artificial Sequence
<220> FEATURE:
<223> OTHER INFORMATION: Synthetic

<400> SEQUENCE: 17
```
caacagtata atagataccc gtggacg                                              27

<210> SEQ ID NO 18
<211> LENGTH: 9
<212> TYPE: PRT
<213> ORGANISM: Artificial Sequence
<220> FEATURE:
<223> OTHER INFORMATION: Synthetic

<400> SEQUENCE: 18

Gln Gln Tyr Asn Arg Tyr Pro Trp Thr
1               5

<210> SEQ ID NO 19
<211> LENGTH: 357
<212> TYPE: DNA
<213> ORGANISM: Artificial Sequence
<220> FEATURE:
<223> OTHER INFORMATION: Synthetic

<400> SEQUENCE: 19
caggtgcagc tggtgcagtc cggcgccgag gtgaagaagc ccggcgcctc cgtgaaggtg      60
tcctgcaagg tgtccggctt caccctgacc gagctgtcca tgcactgggt gcggcaggcc     120
cccggcaagg gcctggagtg gatgggcggc ttcgaccccg aggacggcga gaccatctac     180
gcccagaagt tccagggccg ggtgaccatg accgaggaca cctccaccga caccgcctac     240
atggagctgt cctccctgcg gtccgaggac accgccgtgt actactgctc caccatcttc     300
ggcgtggtga ccaacttcga caactggggc cagggcaccc tggtgaccgt gtcctcc        357

<210> SEQ ID NO 20
<211> LENGTH: 119
<212> TYPE: PRT
<213> ORGANISM: Artificial Sequence
<220> FEATURE:
<223> OTHER INFORMATION: Synthetic

<400> SEQUENCE: 20

Gln Val Gln Leu Val Gln Ser Gly Ala Glu Val Lys Lys Pro Gly Ala
1               5                   10                  15

Ser Val Lys Val Ser Cys Lys Val Ser Gly Phe Thr Leu Thr Glu Leu
            20                  25                  30

Ser Met His Trp Val Arg Gln Ala Pro Gly Lys Gly Leu Glu Trp Met
        35                  40                  45

Gly Gly Phe Asp Pro Glu Asp Gly Glu Thr Ile Tyr Ala Gln Lys Phe
    50                  55                  60

Gln Gly Arg Val Thr Met Thr Glu Asp Thr Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Ser Thr Ile Phe Gly Val Val Thr Asn Phe Asp Asn Trp Gly Gln Gly
            100                 105                 110

Thr Leu Val Thr Val Ser Ser
        115

<210> SEQ ID NO 21
<211> LENGTH: 324
<212> TYPE: DNA
<213> ORGANISM: Artificial Sequence
<220> FEATURE:
<223> OTHER INFORMATION: Synthetic

<400> SEQUENCE: 21

```
gacatccaga tgacccagtc cccctcctcc ctgtccgcct ccgtgggcga ccgggtgacc    60
atcacctgcc gggcctccca ggccatccgg aacgacctgg gctggtacca gcagaagccc   120
ggcaaggccc ccaagcggct gatctacgcc gccttcaacc tgcagtccgg cgtgccctcc   180
cggttctccg gctccggctc cggcaccgag ttcaccctga ccatctcctc cctgcagccc   240
gaggacttcg ccacctacta ctgccagcag tacaaccggt accctggac cttcggccag    300
ggcaccaagg tggagatcaa gcgg                                          324
```

<210> SEQ ID NO 22
<211> LENGTH: 108
<212> TYPE: PRT
<213> ORGANISM: Artificial Sequence
<220> FEATURE:
<223> OTHER INFORMATION: Synthetic

<400> SEQUENCE: 22

```
Asp Ile Gln Met Thr Gln Ser Pro Ser Ser Leu Ser Ala Ser Val Gly
1               5                   10                  15
Asp Arg Val Thr Ile Thr Cys Arg Ala Ser Gln Ala Ile Arg Asn Asp
            20                  25                  30
Leu Gly Trp Tyr Gln Gln Lys Pro Gly Lys Ala Pro Lys Arg Leu Ile
        35                  40                  45
Tyr Ala Ala Phe Asn Leu Gln Ser Gly Val Pro Ser Arg Phe Ser Gly
    50                  55                  60
Ser Gly Ser Gly Thr Glu Phe Thr Leu Thr Ile Ser Ser Leu Gln Pro
65                  70                  75                  80
Glu Asp Phe Ala Thr Tyr Tyr Cys Gln Gln Tyr Asn Arg Tyr Pro Trp
                85                  90                  95
Thr Phe Gly Gln Gly Thr Lys Val Glu Ile Lys Arg
            100                 105
```

<210> SEQ ID NO 23
<211> LENGTH: 357
<212> TYPE: DNA
<213> ORGANISM: Artificial Sequence
<220> FEATURE:
<223> OTHER INFORMATION: Synthetic

<400> SEQUENCE: 23

```
caggtgcagc tggtgcagtc tggggctgag gtgaagaagc ctggggcctc agtgaaggtc    60
tcctgcaagg tttccggatt caccctcact gaattatcca ttcactgggt gcgacaggct   120
cctggaaaag gcttgagtg gatgggaggt tttgatcctg aagatggtga acaatctac    180
gcacagaagt tccagggcag agtcaccatg accgaggaca catctacaga cacagcctac   240
atggagctga ccagcctgag atcggaagac acggccgtgt attactgttc aacgattttt   300
ggagtggtta ccaactttga caactggggc caggaaccc tggtcaccgt ctcctca      357
```

<210> SEQ ID NO 24
<211> LENGTH: 119
<212> TYPE: PRT
<213> ORGANISM: Artificial Sequence
<220> FEATURE:
<223> OTHER INFORMATION: Synthetic

<400> SEQUENCE: 24

```
Gln Val Gln Leu Val Gln Ser Gly Ala Glu Val Lys Lys Pro Gly Ala
1               5                   10                  15
```

-continued

Ser Val Lys Val Ser Cys Lys Val Ser Gly Phe Thr Leu Thr Glu Leu
            20                  25                  30

Ser Ile His Trp Val Arg Gln Ala Pro Gly Lys Gly Leu Glu Trp Met
        35                  40                  45

Gly Gly Phe Asp Pro Glu Asp Gly Glu Thr Ile Tyr Ala Gln Lys Phe
50                  55                  60

Gln Gly Arg Val Thr Met Thr Glu Asp Thr Ser Thr Asp Thr Ala Tyr
65                  70                  75                  80

Met Glu Leu Thr Ser Leu Arg Ser Glu Asp Thr Ala Val Tyr Tyr Cys
                85                  90                  95

Ser Thr Ile Phe Gly Val Val Thr Asn Phe Asp Asn Trp Gly Gln Gly
            100                 105                 110

Thr Leu Val Thr Val Ser Ser
        115

<210> SEQ ID NO 25
<211> LENGTH: 324
<212> TYPE: DNA
<213> ORGANISM: Artificial Sequence
<220> FEATURE:
<223> OTHER INFORMATION: Synthetic

<400> SEQUENCE: 25
gacatccaga tgacccagtc tccatcctcc ctgtctgcat ctgcaggaga cagagtcacc     60
atcacttgcc gggcaagtca ggccattaga aatgatttag ctggtatca gcagaaacca    120 gggaaagccc ctaagcgcct gatctatgct gcattcaatt tgcaaagtgg ggtcccatca    180
agattcagcg gcagtggatc tgggacagaa ttcactctca caatcagtag cctgcagcct    240
gaagatcttg caagttatta ctgtcaacag tataatagat acccgtggac gttcggccaa    300
gggaccaagg tggaaatcaa acga                                           324

<210> SEQ ID NO 26
<211> LENGTH: 108
<212> TYPE: PRT
<213> ORGANISM: Artificial Sequence
<220> FEATURE:
<223> OTHER INFORMATION: Synthetic

<400> SEQUENCE: 26

Asp Ile Gln Met Thr Gln Ser Pro Ser Ser Leu Ser Ala Ser Ala Gly
1               5                   10                  15

Asp Arg Val Thr Ile Thr Cys Arg Ala Ser Gln Ala Ile Arg Asn Asp
            20                  25                  30

Leu Gly Trp Tyr Gln Gln Lys Pro Gly Lys Ala Pro Lys Arg Leu Ile
        35                  40                  45

Tyr Ala Ala Phe Asn Leu Gln Ser Gly Val Pro Ser Arg Phe Ser Gly
50                  55                  60

Ser Gly Ser Gly Thr Glu Phe Thr Leu Thr Ile Ser Ser Leu Gln Pro
65                  70                  75                  80

Glu Asp Leu Ala Ser Tyr Tyr Cys Gln Gln Tyr Asn Arg Tyr Pro Trp
                85                  90                  95

Thr Phe Gly Gln Gly Thr Lys Val Glu Ile Lys Arg
            100                 105

<210> SEQ ID NO 27
<211> LENGTH: 375
<212> TYPE: DNA

<210> ORGANISM: Artificial Sequence
<220> FEATURE:
<223> OTHER INFORMATION: Synthetic

<400> SEQUENCE: 27

```
gaagtgcagc tggtgcagtc tgggggcggc ttggtacagc ctggcaggtc cctgagactc    60
tcctgtgcag ccctggatt caactttgat gattatgcca tgcactgggt ccggcaaact    120
ccagggaagg gcctggagtg gtctcaggt attagttgga atagtggtac tataggctat    180
gcggactctg tgaagggccg attaccatc tccagagaca acgccaagaa ctccctgtat    240
cttcaaatga acagtctgag acctgaggac acggccttgt attactgtgc aaaagaaggg    300
gtatggttcg gaaaattgtt ctcatcctac ggtatggacg tctggggcca agggaccacg    360
gtcaccgtct cctca                                                    375
```

<210> SEQ ID NO 28
<211> LENGTH: 125
<212> TYPE: PRT
<213> ORGANISM: Artificial Sequence
<220> FEATURE:
<223> OTHER INFORMATION: Synthetic

<400> SEQUENCE: 28

```
Glu Val Gln Leu Val Gln Ser Gly Gly Gly Leu Val Gln Pro Gly Arg
1               5                   10                  15

Ser Leu Arg Leu Ser Cys Ala Ala Pro Gly Phe Asn Phe Asp Asp Tyr
            20                  25                  30

Ala Met His Trp Val Arg Gln Thr Pro Gly Lys Gly Leu Glu Trp Val
        35                  40                  45

Ser Gly Ile Ser Trp Asn Ser Gly Thr Ile Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Pro Glu Asp Thr Ala Leu Tyr Tyr Cys
                85                  90                  95

Ala Lys Glu Gly Val Trp Phe Gly Lys Leu Phe Ser Ser Tyr Gly Met
            100                 105                 110

Asp Val Trp Gly Gln Gly Thr Thr Val Thr Val Ser Ser
        115                 120                 125
```

<210> SEQ ID NO 29
<211> LENGTH: 24
<212> TYPE: DNA
<213> ORGANISM: Artificial Sequence
<220> FEATURE:
<223> OTHER INFORMATION: Synthetic

<400> SEQUENCE: 29

```
ggattcaact ttgatgatta tgcc                                          24
```

<210> SEQ ID NO 30
<211> LENGTH: 8
<212> TYPE: PRT
<213> ORGANISM: Artificial Sequence
<220> FEATURE:
<223> OTHER INFORMATION: Synthetic

<400> SEQUENCE: 30

```
Gly Phe Asn Phe Asp Asp Tyr Ala
1               5
```

<210> SEQ ID NO 31
<211> LENGTH: 24
<212> TYPE: DNA
<213> ORGANISM: Artificial Sequence
<220> FEATURE:
<223> OTHER INFORMATION: Synthetic

<400> SEQUENCE: 31
attagttgga atagtggtac tata                                         24

<210> SEQ ID NO 32
<211> LENGTH: 8
<212> TYPE: PRT
<213> ORGANISM: Artificial Sequence
<220> FEATURE:
<223> OTHER INFORMATION: Synthetic

<400> SEQUENCE: 32

Ile Ser Trp Asn Ser Gly Thr Ile
1               5

<210> SEQ ID NO 33
<211> LENGTH: 54
<212> TYPE: DNA
<213> ORGANISM: Artificial Sequence
<220> FEATURE:
<223> OTHER INFORMATION: Synthetic

<400> SEQUENCE: 33
gcaaaagaag gggtatggtt cggaaaattg ttctcatcct acggtatgga cgtc         54

<210> SEQ ID NO 34
<211> LENGTH: 18
<212> TYPE: PRT
<213> ORGANISM: Artificial Sequence
<220> FEATURE:
<223> OTHER INFORMATION: Synthetic

<400> SEQUENCE: 34

Ala Lys Glu Gly Val Trp Phe Gly Lys Leu Phe Ser Ser Tyr Gly Met
1               5                   10                  15

Asp Val

<210> SEQ ID NO 35
<211> LENGTH: 321
<212> TYPE: DNA
<213> ORGANISM: Artificial Sequence
<220> FEATURE:
<223> OTHER INFORMATION: Synthetic

<400> SEQUENCE: 35
gacatccgga tgacccagtc tccagccacc ctgtctgtgt ctccagggga aagagccacc    60
ctctcctgca gggccagtca gagtgttact tacaacttag actggtacca gcagaaacct   120
ggccaggctc ccaggctcct catctttggt gcatccacca gggccactgg tatcccagcc   180
aggttcagtg gcagtgggtc tgggacagag ttcactctca ccatcaccag cctgcagtct   240
gaagattttg cagtttatta ctgtcagcag tataataact ggccgtacac ttttggccag   300
gggaccaagg tggaaatcaa a                                             321

<210> SEQ ID NO 36
<211> LENGTH: 107
<212> TYPE: PRT
<213> ORGANISM: Artificial Sequence
<220> FEATURE:
<223> OTHER INFORMATION: Synthetic

<400> SEQUENCE: 36

Asp Ile Arg Met Thr Gln Ser Pro Ala Thr Leu Ser Val Ser Pro Gly
1               5                   10                  15

Glu Arg Ala Thr Leu Ser Cys Arg Ala Ser Gln Ser Val Thr Tyr Asn
            20                  25                  30

Leu Asp Trp Tyr Gln Gln Lys Pro Gly Gln Ala Pro Arg Leu Leu Ile
        35                  40                  45

Phe Gly Ala Ser Thr Arg Ala Thr Gly Ile Pro Ala Arg Phe Ser Gly
50                  55                  60

Ser Gly Ser Gly Thr Glu Phe Thr Leu Thr Ile Thr Ser Leu Gln Ser
65                  70                  75                  80

Glu Asp Phe Ala Val Tyr Tyr Cys Gln Gln Tyr Asn Asn Trp Pro Tyr
                85                  90                  95

Thr Phe Gly Gln Gly Thr Lys Val Glu Ile Lys
            100                 105

<210> SEQ ID NO 37
<211> LENGTH: 18
<212> TYPE: DNA
<213> ORGANISM: Artificial Sequence
<220> FEATURE:
<223> OTHER INFORMATION: Synthetic

<400> SEQUENCE: 37
cagagtgtta cttacaac                                                 18

<210> SEQ ID NO 38
<211> LENGTH: 6
<212> TYPE: PRT
<213> ORGANISM: Artificial Sequence
<220> FEATURE:
<223> OTHER INFORMATION: Synthetic

<400> SEQUENCE: 38

Gln Ser Val Thr Tyr Asn
1               5

<210> SEQ ID NO 39
<211> LENGTH: 9
<212> TYPE: DNA
<213> ORGANISM: Artificial Sequence
<220> FEATURE:
<223> OTHER INFORMATION: Synthetic

<400> SEQUENCE: 39 ggtgcatcc                                                            9

<210> SEQ ID NO 40
<211> LENGTH: 3
<212> TYPE: PRT
<213> ORGANISM: Artificial Sequence
<220> FEATURE:
<223> OTHER INFORMATION: Synthetic

<400> SEQUENCE: 40

Gly Ala Ser
1

<210> SEQ ID NO 41
<211> LENGTH: 27

<210> SEQ ID NO 41
<211> LENGTH: 27
<212> TYPE: DNA
<213> ORGANISM: Artificial Sequence
<220> FEATURE:
<223> OTHER INFORMATION: Synthetic

<400> SEQUENCE: 41
cagcagtata ataactggcc gtacact                                         27

<210> SEQ ID NO 42
<211> LENGTH: 9
<212> TYPE: PRT
<213> ORGANISM: Artificial Sequence
<220> FEATURE:
<223> OTHER INFORMATION: Synthetic

<400> SEQUENCE: 42

Gln Gln Tyr Asn Asn Trp Pro Tyr Thr
1               5

<210> SEQ ID NO 43
<211> LENGTH: 375
<212> TYPE: DNA
<213> ORGANISM: Artificial Sequence
<220> FEATURE:
<223> OTHER INFORMATION: Synthetic

<400> SEQUENCE: 43
gaggtgcagc tggtggagtc cggcggcggc ctggtgcagc ccggccggtc cctgcggctg      60
tcctgcgccg cccccggctt caacttcgac gactacgcca tgcactgggt gcggcaggcc     120
cccggcaagg gcctggagtg gtgtccggc atctcctgga actccggcac catcggctac      180
gccgactccg tgaagggccg gttcaccatc tcccgggaca cgccaagaa ctccctgtac      240 ctgcagatga actccctgcg ggccgaggac accgccctgt actactgcgc caaggagggc     300
gtgtggttcg gcaagctgtt ctcctcctac ggcatggacg tgtggggcca gggcaccacc     360
gtgaccgtgt cctcc                                                     375

<210> SEQ ID NO 44
<211> LENGTH: 125
<212> TYPE: PRT
<213> ORGANISM: Artificial Sequence
<220> FEATURE:
<223> OTHER INFORMATION: Synthetic

<400> SEQUENCE: 44

Glu Val Gln Leu Val Glu Ser Gly Gly Gly Leu Val Gln Pro Gly Arg
1               5                   10                  15

Ser Leu Arg Leu Ser Cys Ala Ala Pro Gly Phe Asn Phe Asp Asp Tyr
            20                  25                  30

Ala Met His Trp Val Arg Gln Ala Pro Gly Lys Gly Leu Glu Trp Val
        35                  40                  45

Ser Gly Ile Ser Trp Asn Ser Gly Thr Ile Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Lys Glu Gly Val Trp Phe Gly Lys Leu Phe Ser Ser Tyr Gly Met
            100                 105                 110

Asp Val Trp Gly Gln Gly Thr Thr Val Thr Val Ser Ser
        115                 120                 125

<210> SEQ ID NO 45
<211> LENGTH: 324
<212> TYPE: DNA
<213> ORGANISM: Artificial Sequence
<220> FEATURE:
<223> OTHER INFORMATION: Synthetic

<400> SEQUENCE: 45

```
gagatcgtga tgacccagtc ccccgccacc ctgtccgtgt ccccccggcga gcgggccacc    60 ctgtcctgcc gggcctccca gtccgtgacc tacaacctgg actggtacca gcagaagccc   120
ggccaggccc cccggctgct gatctacggc gcctccaccc gggccaccgg catccccgcc   180
cggttctccg gctccggctc cggcaccgag ttcaccctga ccatctcctc cctgcagtcc   240
gaggacttcg ccgtgtacta ctgccagcag tacaacaact ggccctacac cttcggccag   300
ggcaccaagc tggagatcaa gcgg                                          324
```

<210> SEQ ID NO 46
<211> LENGTH: 108
<212> TYPE: PRT
<213> ORGANISM: Artificial Sequence
<220> FEATURE:
<223> OTHER INFORMATION: Synthetic

<400> SEQUENCE: 46

```
Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Thr Tyr Asn
            20                  25                  30

Leu Asp Trp Tyr Gln Gln Lys Pro Gly Gln Ala Pro Arg Leu Leu Ile
        35                  40                  45

Tyr Gly Ala Ser Thr Arg Ala Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Asn Asn Trp Pro Tyr
                85                  90                  95

Thr Phe Gly Gln Gly Thr Lys Leu Glu Ile Lys Arg
            100                 105
```

<210> SEQ ID NO 47
<211> LENGTH: 375
<212> TYPE: DNA
<213> ORGANISM: Artificial Sequence
<220> FEATURE:
<223> OTHER INFORMATION: Synthetic

<400> SEQUENCE: 47

```
gaagtgcagc tggtggagtc tgggggcggc ttggtacagc ctggcaggtc cctgagactc     60
tcctgtgcag cccctggatt caactttgat gattatgcca tgcactgggt ccggcaaact    120
ccagggaagg gcctggagtg ggtctcaggt attagttgga atagtggtac tataggctat    180
gcggactctg tgaagggccg atttaccatc tccagagaca acgccaagaa ctccctgtat    240
cttcaaatga acagtctgag acctgaggac acggccttgt attactgtgc aaaagaaggg    300
gtatggttcg gaaaattgtt ctcatcctac ggtatggacg tctggggcca agggaccacg    360
gtcaccgtct cctca                                                    375
```

<210> SEQ ID NO 48
<211> LENGTH: 125
<212> TYPE: PRT
<213> ORGANISM: Artificial Sequence
<220> FEATURE:
<223> OTHER INFORMATION: Synthetic

<400> SEQUENCE: 48

```
Glu Val Gln Leu Val Glu Ser Gly Gly Gly Leu Val Gln Pro Gly Arg
1               5                   10                  15

Ser Leu Arg Leu Ser Cys Ala Ala Pro Gly Phe Asn Phe Asp Asp Tyr
            20                  25                  30

Ala Met His Trp Val Arg Gln Thr Pro Gly Lys Gly Leu Glu Trp Val
        35                  40                  45

Ser Gly Ile Ser Trp Asn Ser Gly Thr Ile Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Pro Glu Asp Thr Ala Leu Tyr Tyr Cys
                85                  90                  95

Ala Lys Glu Gly Val Trp Phe Gly Lys Leu Phe Ser Ser Tyr Gly Met
            100                 105                 110

Asp Val Trp Gly Gln Gly Thr Thr Val Thr Val Ser Ser
        115                 120                 125
```

<210> SEQ ID NO 49
<211> LENGTH: 324
<212> TYPE: DNA
<213> ORGANISM: Artificial Sequence
<220> FEATURE:
<223> OTHER INFORMATION: Synthetic

<400> SEQUENCE: 49

```
gaaatagtga tgacgcagtc tccagccacc ctgtctgtgt ctccagggga aagagccacc    60
ctctcctgca gggccagtca gagtgttact tacaacttag actggtacca gcagaaacct   120
ggccaggctc ccaggctcct catctttggt gcatccacca gggccactgg tatcccagcc   180
aggttcagtg gcagtgggtc tgggacagag ttcactctca ccatcaccag cctgcagtct   240
gaagattttg cagtttatta ctgtcagcag tataataact ggccgtacac ttttggccag   300
gggaccaagc tggagatcaa acga                                          324
```

<210> SEQ ID NO 50
<211> LENGTH: 108
<212> TYPE: PRT
<213> ORGANISM: Artificial Sequence
<220> FEATURE:
<223> OTHER INFORMATION: Synthetic

<400> SEQUENCE: 50

```
Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Thr Tyr Asn
            20                  25                  30

Leu Asp Trp Tyr Gln Gln Lys Pro Gly Gln Ala Pro Arg Leu Leu Ile
        35                  40                  45

Phe Gly Ala Ser Thr Arg Ala Thr Gly Ile Pro Ala Arg Phe Ser Gly
    50                  55                  60

Ser Gly Ser Gly Thr Glu Phe Thr Leu Thr Ile Thr Ser Leu Gln Ser
65                  70                  75                  80
```

Glu Asp Phe Ala Val Tyr Tyr Cys Gln Gln Tyr Asn Asn Trp Pro Tyr
                85                  90                  95

Thr Phe Gly Gln Gly Thr Lys Leu Glu Ile Lys Arg
            100                 105

<210> SEQ ID NO 51
<211> LENGTH: 8
<212> TYPE: PRT
<213> ORGANISM: Artificial Sequence
<220> FEATURE:
<223> OTHER INFORMATION: Synthetic
<220> FEATURE:
<221> NAME/KEY: VARIANT
<222> LOCATION: (1)...(1)
<223> OTHER INFORMATION: Xaa = Gly
<220> FEATURE:
<221> NAME/KEY: VARIANT
<222> LOCATION: (2)...(2)
<223> OTHER INFORMATION: Xaa = Phe
<220> FEATURE:
<221> NAME/KEY: VARIANT
<222> LOCATION: (3)...(3)
<223> OTHER INFORMATION: Xaa = Thr or Asn
<220> FEATURE:
<221> NAME/KEY: VARIANT
<222> LOCATION: (4)...(4)
<223> OTHER INFORMATION: Xaa = Phe or Leu
<220> FEATURE:
<221> NAME/KEY: VARIANT
<222> LOCATION: (5)...(5)
<223> OTHER INFORMATION: Xaa = Thr or Asp
<220> FEATURE:
<221> NAME/KEY: VARIANT
<222> LOCATION: (6)...(6)
<223> OTHER INFORMATION: Xaa = Asp or Glu
<220> FEATURE:
<221> NAME/KEY: VARIANT
<222> LOCATION: (7)...(7)
<223> OTHER INFORMATION: Xaa = Tyr or Leu
<220> FEATURE:
<221> NAME/KEY: VARIANT
<222> LOCATION: (8)...(8)
<223> OTHER INFORMATION: Xaa = Ser or Ala

<400> SEQUENCE: 51

Xaa Xaa Xaa Xaa Xaa Xaa Xaa Xaa
1               5

<210> SEQ ID NO 52
<211> LENGTH: 8
<212> TYPE: PRT
<213> ORGANISM: Artificial Sequence
<220> FEATURE:
<223> OTHER INFORMATION: Synthetic
<220> FEATURE:
<221> NAME/KEY: VARIANT
<222> LOCATION: (1)...(1)
<223> OTHER INFORMATION: Xaa = Ile or Phe
<220> FEATURE:
<221> NAME/KEY: VARIANT
<222> LOCATION: (2)...(2)
<223> OTHER INFORMATION: Xaa = Asp or Ser
<220> FEATURE:
<221> NAME/KEY: VARIANT
<222> LOCATION: (3)...(3)
<223> OTHER INFORMATION: Xaa = Pro or Trp
<220> FEATURE:
<221> NAME/KEY: VARIANT
<222> LOCATION: (4)...(4)
<223> OTHER INFORMATION: Xaa = Glu or Asn
<220> FEATURE:
<221> NAME/KEY: VARIANT
<222> LOCATION: (5)...(5)
<223> OTHER INFORMATION: Xaa = Asp or Ser

```
<220> FEATURE:
<221> NAME/KEY: VARIANT
<222> LOCATION: (6)...(6)
<223> OTHER INFORMATION: Xaa = Gly
<220> FEATURE:
<221> NAME/KEY: VARIANT
<222> LOCATION: (7)...(7)
<223> OTHER INFORMATION: Xaa = Thr or Glu
<220> FEATURE:
<221> NAME/KEY: VARIANT
<222> LOCATION: (8)...(8)
<223> OTHER INFORMATION: Xaa = Thr or Ile

<400> SEQUENCE: 52

Xaa Xaa Xaa Xaa Xaa Xaa Xaa Xaa
1               5

<210> SEQ ID NO 53
<211> LENGTH: 18
<212> TYPE: PRT
<213> ORGANISM: Artificial Sequence
<220> FEATURE:
<223> OTHER INFORMATION: Synthetic
<220> FEATURE:
<221> NAME/KEY: VARIANT
<222> LOCATION: (1)...(1)
<223> OTHER INFORMATION: Xaa = Ala or Ser
<220> FEATURE:
<221> NAME/KEY: VARIANT
<222> LOCATION: (2)...(2)
<223> OTHER INFORMATION: Xaa = Thr or Lys
<220> FEATURE:
<221> NAME/KEY: VARIANT
<222> LOCATION: (3)...(3)
<223> OTHER INFORMATION: Xaa = Glu or Ile
<220> FEATURE:
<221> NAME/KEY: VARIANT
<222> LOCATION: (4)...(4)
<223> OTHER INFORMATION: Xaa = Phe or Gly
<220> FEATURE:
<221> NAME/KEY: VARIANT
<222> LOCATION: (5)...(5)
<223> OTHER INFORMATION: Xaa = Val or Gly
<220> FEATURE:
<221> NAME/KEY: VARIANT
<222> LOCATION: (6)...(6)
<223> OTHER INFORMATION: Xaa = Val or Trp
<220> FEATURE:
<221> NAME/KEY: VARIANT
<222> LOCATION: (7)...(7)
<223> OTHER INFORMATION: Xaa = Val or Phe
<220> FEATURE:
<221> NAME/KEY: VARIANT
<222> LOCATION: (8)...(8)
<223> OTHER INFORMATION: Xaa = Thr or Gly
<220> FEATURE:
<221> NAME/KEY: VARIANT
<222> LOCATION: (9)...(9)
<223> OTHER INFORMATION: Xaa = Asn or Lys
<220> FEATURE:
<221> NAME/KEY: VARIANT
<222> LOCATION: (10)...(10)
<223> OTHER INFORMATION: Xaa = Phe or Leu
<220> FEATURE:
<221> NAME/KEY: VARIANT
<222> LOCATION: (11)...(11)
<223> OTHER INFORMATION: Xaa = Asp or Phe
<220> FEATURE:
<221> NAME/KEY: VARIANT
<222> LOCATION: (12)...(12)
<223> OTHER INFORMATION: Xaa = Asn or Ser
<220> FEATURE:
<221> NAME/KEY: VARIANT
<222> LOCATION: (13)...(13)
<223> OTHER INFORMATION: Xaa = Ser or absent
<220> FEATURE:
<221> NAME/KEY: VARIANT
```

```
<222> LOCATION: (14)...(14)
<223> OTHER INFORMATION: Xaa = Tyr or absent
<220> FEATURE:
<221> NAME/KEY: VARIANT
<222> LOCATION: (15)...(15)
<223> OTHER INFORMATION: Xaa = Gly or absent
<220> FEATURE:
<221> NAME/KEY: VARIANT
<222> LOCATION: (16)...(16)
<223> OTHER INFORMATION: Xaa = Met or absent
<220> FEATURE:
<221> NAME/KEY: VARIANT
<222> LOCATION: (17)...(17)
<223> OTHER INFORMATION: Xaa = Asp or absent
<220> FEATURE:
<221> NAME/KEY: VARIANT
<222> LOCATION: (18)...(18)
<223> OTHER INFORMATION: Xaa = Val or absent

<400> SEQUENCE: 53

Xaa Xaa Xaa Xaa Xaa Xaa Xaa Xaa Xaa Xaa Xaa Xaa Xaa Xaa Xaa Xaa
1               5                   10                  15

Xaa Xaa

<210> SEQ ID NO 54
<211> LENGTH: 6
<212> TYPE: PRT
<213> ORGANISM: Artificial Sequence
<220> FEATURE:
<223> OTHER INFORMATION: Synthetic
<220> FEATURE:
<221> NAME/KEY: VARIANT
<222> LOCATION: (1)...(1)
<223> OTHER INFORMATION: Xaa = Gln
<220> FEATURE:
<221> NAME/KEY: VARIANT
<222> LOCATION: (2)...(2)
<223> OTHER INFORMATION: Xaa = Ala or Ser
<220> FEATURE:
<221> NAME/KEY: VARIANT
<222> LOCATION: (3)...(3)
<223> OTHER INFORMATION: Xaa = Val or Ile
<220> FEATURE:
<221> NAME/KEY: VARIANT
<222> LOCATION: (4)...(4)
<223> OTHER INFORMATION: Xaa = Arg or Thr
<220> FEATURE:
<221> NAME/KEY: VARIANT
<222> LOCATION: (5)...(5)
<223> OTHER INFORMATION: Xaa = Asn or Tyr
<220> FEATURE:
<221> NAME/KEY: VARIANT
<222> LOCATION: (6)...(6)
<223> OTHER INFORMATION: Xaa = Asp or Asn

<400> SEQUENCE: 54

Xaa Xaa Xaa Xaa Xaa Xaa
1               5

<210> SEQ ID NO 55
<211> LENGTH: 3
<212> TYPE: PRT
<213> ORGANISM: Artificial Sequence
<220> FEATURE:
<223> OTHER INFORMATION: Synthetic
<220> FEATURE:
<221> NAME/KEY: VARIANT
<222> LOCATION: (1)...(1)
<223> OTHER INFORMATION: Xaa = Gly or Ala
<220> FEATURE:
<221> NAME/KEY: VARIANT
<222> LOCATION: (2)...(2)
<223> OTHER INFORMATION: Xaa = Ala
<220> FEATURE:
```

```
<221> NAME/KEY: VARIANT
<222> LOCATION: (3)...(3)
<223> OTHER INFORMATION: Xaa = Ser or Phe

<400> SEQUENCE: 55

Xaa Xaa Xaa
1

<210> SEQ ID NO 56
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: VARIANT
<222> LOCATION: (1)...(1)
<223> OTHER INFORMATION: Xaa = Gln
<220> FEATURE:
<221> NAME/KEY: VARIANT
<222> LOCATION: (2)...(2)
<223> OTHER INFORMATION: Xaa = Gln
<220> FEATURE:
<221> NAME/KEY: VARIANT
<222> LOCATION: (3)...(3)
<223> OTHER INFORMATION: Xaa = Tyr
<220> FEATURE:
<221> NAME/KEY: VARIANT
<222> LOCATION: (4)...(4)
<223> OTHER INFORMATION: Xaa = Asn
<220> FEATURE:
<221> NAME/KEY: VARIANT
<222> LOCATION: (5)...(5)
<223> OTHER INFORMATION: Xaa = Arg or Asn
<220> FEATURE:
<221> NAME/KEY: VARIANT
<222> LOCATION: (6)...(6)
<223> OTHER INFORMATION: Xaa = Tyr or Trp
<220> FEATURE:
<221> NAME/KEY: VARIANT
<222> LOCATION: (7)...(7)
<223> OTHER INFORMATION: Xaa = Pro
<220> FEATURE:
<221> NAME/KEY: VARIANT
<222> LOCATION: (8)...(8)
<223> OTHER INFORMATION: Xaa = Tyr or Trp
<220> FEATURE:
<221> NAME/KEY: VARIANT
<222> LOCATION: (9)...(9)
<223> OTHER INFORMATION: Xaa = Thr

<400> SEQUENCE: 56

Xaa Xaa Xaa Xaa Xaa Xaa Xaa Xaa Xaa
1               5

<210> SEQ ID NO 57
<211> LENGTH: 330
<212> TYPE: PRT
<213> ORGANISM: Artificial Sequence
<220> FEATURE:
<223> OTHER INFORMATION: Synthetic

<400> SEQUENCE: 57

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60
```

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 58
<211> LENGTH: 327
<212> TYPE: PRT
<213> ORGANISM: Artificial Sequence
<220> FEATURE:
<223> OTHER INFORMATION: Synthetic

<400> SEQUENCE: 58

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Lys Thr
65                  70                  75                  80

Tyr Thr Cys Asn Val Asp His Lys Pro Ser Asn Thr Lys Val Asp Lys
                85                  90                  95

```
Arg Val Glu Ser Lys Tyr Gly Pro Pro Cys Pro Ser Cys Pro Ala Pro
            100                 105                 110

Glu Phe Leu Gly Gly Pro Ser Val Phe Leu Phe Pro Pro Lys Pro Lys
            115                 120                 125

Asp Thr Leu Met Ile Ser Arg Thr Pro Glu Val Thr Cys Val Val Val
130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
            195                 200                 205

Pro Ser Ser Ile Glu Lys Thr Ile Ser Lys Ala Lys Gly Gln Pro Arg
210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
            275                 280                 285

Arg Leu Thr Val Asp Lys Ser Arg Trp Gln Glu Gly Asn Val Phe Ser
            290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 59
<211> LENGTH: 327
<212> TYPE: PRT
<213> ORGANISM: Artificial Sequence
<220> FEATURE:
<223> OTHER INFORMATION: Synthetic

<400> SEQUENCE: 59

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Glu Phe Leu Gly Gly Pro Ser Val Phe Leu Phe Pro Pro Lys Pro Lys
            115                 120                 125
```

```
Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
                180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
                260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly Lys
                325
```

METHOD OF TREATING OSTEOARTHRITIS WITH AN ANTIBODY TO NGF

FIELD OF THE INVENTION

The present invention is related to therapeutic methods for treating osteoarthritis in a human patient in need thereof, with an antibody or antigen-binding fragment of an antibody specific for human nerve growth factor (NGF) and pharmaceutical compositions containing the antibody or antibody fragment.

STATEMENT OF RELATED ART

While numerous analgesic medications are currently available, the adequate relief of pain remains an unmet medical need for many acute and chronic pain states. The limitations of currently available analgesic therapies include adverse central nervous system (CNS) effects, nausea and vomiting, gastrointestinal (GI) bleeding and ulceration, idiosyncratic cardiovascular events attributed to drugs that suppress cyclooxygenase-2, renal toxicity, abuse potential and others that span the spectrum of drug toxicity.

Osteoarthritis is a progressive, chronic disease in which pain is often a key limiting factor and for which acceptable long-term therapy does not yet exist. Current long-term therapies such as non-steroidal anti-inflammatory drugs (NSAIDs) and celecoxib can be problematic due to specific side effects and potential health risks such as GI bleeding and increased risk of cardiovascular events. In addition, these medications must be taken daily to maintain their analgesic effects. As the prevalence of OA in patients aged older than 65 years is 60% in men and 70% in women and continually rising, the search for additional treatment options with fewer associated side-effects is ongoing.

Neurotrophins are a family of peptide growth factors that play a role in the development, differentiation, survival and death of neuronal and non-neuronal cells. The first neurotrophin to be identified was nerve growth factor (NGF), and its role in the development and survival of both peripheral and central neurons during the developing nervous system has been well characterized. In the adult, NGF is a pain mediator that sensitizes neurons and is not required as a survival factor.

NGF activity is mediated through two different membrane-bound receptors, the TrkA receptor and the p75 common neurotrophin receptor. The NGF/TrkA system appears to play a major role in the control of inflammation and pain, since it is upstream of several relevant molecular pathways. Mast cells, for example, are capable of producing NGF, but are also induced by NGF to release inflammatory mediators. Nerve growth factor expression is known to be upregulated in injured and inflamed tissues in conditions such as cystitis, prostatitis, and chronic headache.

Selective antagonism of NGF by a fully-human high-affinity monoclonal antibody (mAb) has the potential to be effective without the adverse side effects of traditional analgesic drugs, since it works through a different physiological mechanism of action. Human genetic studies that show that people suffering from a loss of deep pain perception have mutations in TrkA (HSAN IV) or NGF (HSAN V). In addition, NGF is known to be elevated in the synovial fluid of patients suffering from rheumatoid arthritis and other types of arthritis.

Anti-NGF antibodies are described in, for example, EP1575517; WO 01/78698, WO 02/096458, WO 2004/032870; U.S. Pat. Nos. 7,601,818; 7,449,616; 7,655,232; US patent application publications 2009/0155274; 2009/0208490; 2008/033157; 2008/0107658; 2005/0074821; 2004/0237124, and 2004/0219144.

BRIEF SUMMARY OF THE INVENTION

In a first aspect, the invention features methods for preventing, inhibiting, ameliorating and/or treating at least one of the symptoms associated with osteoarthritis in a human subject in need thereof, comprising administering to the subject a therapeutically effective amount of a fully human anti-NGF antibody, or antigen-binding fragment thereof, wherein at least one of the symptoms of osteoarthritis is prevented, inhibited, ameliorated or improved. In specific embodiments, the antibody or antigen-binding fragment of an antibody to be used in the method of the invention is a fully human antibody comprising heavy chain variable region (HCVR) selected from the group consisting of SEQ ID NO: 4, 20, 24, 28, 44 and 48. In more specific embodiments, the HCVR is selected from the group of SEQ ID NO: 20, 24 and 48. In one specific embodiment, the HCVR is SEQ ID NO:24. In specific embodiments, the antibody or antigen-binding fragment thereof to be used in the present invention is a fully human antibody comprising light chain variable region (LCVR) selected from the group consisting of SEQ ID NO: 12, 22, 26, 36, 46 and 50. In more specific embodiments, the LCVR is selected from the group of SEQ ID NO: 22, 26 and 50. In one specific embodiment, the LCVR is SEQ ID NO:26.

In specific embodiments, the antibody or fragment thereof comprises a HCVR and LCVR (HCVR/LCVR) sequence pair selected from the group consisting of SEQ ID NO: 4/12, 20/22, 24/26, 28/36, 44/46 and 48/50. In more specific embodiments, the HCVR/LCVR sequence pair is selected from the group consisting of SEQ ID NO: 20/22, 24/26 and 48/50. In one specific embodiment, the HCVR/LCVR sequence pair is SEQ ID NO:24/26.

In a second aspect, the invention features a method of treating, inhibiting, ameliorating, or reducing the occurrence of osteoarthritis in a human subject in need thereof, comprising administering to the subject a therapeutically effective amount of an anti-human NGF antibody or antigen-binding fragment thereof, wherein the antibody or antigen-binding fragment thereof comprises heavy and light chain complementary determining regions (HCDR and LCDR) from HCVR/LCVR sequence pairs selected from the group consisting of SEQ ID NO: 4/12, 20/22, 24/26, 28/36, 44/46 and 48/50. In more specific embodiments, the antibody or antibody fragment comprise CDRs from HCVR/LCVR sequence pairs selected from the group consisting of SEQ ID NO: 20/22, 24/26 and 48/50. In one specific embodiment, the CDRs are from the sequence pair of SEQ ID NO: 24/26. Methods and techniques for identifying CDRs within HCVR and LCVR amino acid sequences are well known in the art and can be used to identify CDRs within the specified HCVR and/or LCVR amino acid sequences disclosed herein. Exemplary conventions that can be used to identify the boundaries of CDRs include, e.g., the Kabat definition, the Chothia definition, and the AbM definition. In general terms, the Kabat definition is based on sequence variability, the Chothia definition is based on the location of the structural loop regions, and the AbM definition is a compromise between the Kabat and Chothia approaches. See, e.g., Kabat, "Sequences of Proteins of Immunological Interest," National Institutes of Health, Bethesda, Md. (1991); Al-Lazikani et al., *J. Mol. Biol.* 273:927-948 (1997); and Martin et al., *Proc. Natl. Acad. Sci. USA* 86:9268-9272

(1989). Public databases are also available for identifying CDR sequences within an antibody.

In one embodiment, the antibody or antigen-binding fragment thereof comprises a heavy chain CDR3 (HCDR3) and a light chain CDR3 (LCDR3), wherein the HCDR3 comprises an amino acid sequence of the formula $X^1$-$X^2$-$X^3$-$X^4$-$X^5$-$X^6$-$X^7$-$X^8$-$X^9$-$X^{10}$-$X^{11}$-$X^{12}$-$X^{13}$-$X^{14}$-$X^{15}$-$X^{16}$-$X^{17}$-$X^{18}$ (SEQ ID NO:53) wherein $X^1$ is Ala or Ser, $X^2$ is Thr or Lys, $X^3$ is Glu or Ile, $X^4$ is Phe or Gly, $X^5$ is Val or Gly, $X^6$ is Val or Trp, $X^7$ is Val or Phe, $X^8$ is Thr or Gly, $X^9$ is Asn or Lys, $X^{10}$ is Phe or Leu, $X^{11}$ is Asp or Phe, $X^{12}$ is Asn or Ser, $X^{13}$ is Ser or absent, $X^{14}$ is Tyr or absent, $X^{15}$ is Gly or absent, $X^{16}$ is Met or absent, $X^{17}$ is Asp or absent, and $X^{18}$ is Val or absent; and the LCDR3 comprises an amino acid sequence of the formula $X^1$-$X^2$-$X^3$-$X^4$-$X^5$-$X^6$-$X^7$-$X^8$-$X^9$ (SEQ ID NO:56) wherein $X^1$ is Gln, $X^2$ is Gln, $X^3$ is Tyr, $X^4$ is Asn, $X^5$ is Arg or Asn, $X^6$ is Tyr or Trp, $X^7$ is Pro, $X^8$ is Tyr or Trp, and $X^9$ is Thr.

In another embodiment, the antibody or antigen binding fragment thereof further comprises a HCDR1 sequence comprising the formula $X^1$-$X^2$-$X^3$-$X^4$-$X^5$-$X^6$-$X^7$-$X^8$ (SEQ ID NO:51), wherein $X^1$ is Gly, $X^2$ is Phe, $X^3$ is Thr or Asn, $X^4$ is Phe or Leu, $X^5$ is Thr or Asp, $X^6$ is Asp or Glu, $X^7$ is Tyr or Leu, and $X^8$ is Ser or Ala; a HCDR2 sequence comprising the formula $X^1$-$X^2$-$X^3$-$X^4$-$X^5$-$X^6$-$X^7$-$X^8$ (SEQ ID NO:52), wherein $X^1$ is Ile or Phe, $X^2$ is Asp or Ser, $X^3$ is Pro or Trp, $X^4$ is Glu or Asn, $X^5$ is Asp or Ser, $X^6$ is Gly, $X^7$ is Thr or Glu, $X^8$ is Thr or Ile; a LCDR1 sequence comprising the formula $X^1$-$X^2$-$X^3$-$X^4$-$X^5$-$X^6$ (SEQ ID NO:54) wherein $X^1$ is Gln, $X^2$ is Ala or Ser, $X^3$ is Val or Ile, $X^4$ is Arg or Thr, $X^5$ is Asn or Tyr, and $X^6$ is Asp or Asn; and a LCDR2 sequence comprising the formula $X^1$-$X^2$-$X^3$ (SEQ ID NO:55) wherein $X^1$ is Gly or Ala, $X^2$ is Ala, and $X^3$ is Ser or Phe.

In a third aspect, the invention features a method of treating, inhibiting or ameliorating osteoarthritis in a subject in need thereof, or at least one symptom associated with osteoarthritis, comprising administering to the subject a therapeutically effective amount an antibody or antigen-binding fragment thereof comprising a HCDR3 selected from the group consisting of SEQ ID NO: 10 and 34, and a LCDR3 selected from the group consisting of SEQ ID NO: 18 and 42. In a more specific embodiment, the HCDR3/LCDR3 are selected from the sequence pair groups consisting of SEQ ID NO: 10/18 and 34/42.

In a further embodiment, the antibody or fragment thereof comprises heavy chain CDRs (HCDR1, HCDR2 and HCDR3) and light chain CDRs (LCDR1, LCDR2 and LCDR3) selected from the group consisting of SEQ ID NO: 6, 8, 10, 30, 32, 34; and 14, 16, 18, 38, 40, 42, respectively. In one embodiment, the antibody or fragment thereof comprises CDR sequences SEQ ID NO: 6, 8, 10, 14, 16 and 18.

In various embodiments of a method of the invention, administration of the antibody or antigen-binding fragment of an antibody is by, for example, subcutaneous or intravenous administration, or administration locally at the site of disease. In one embodiment, the In a fourth aspect, the invention features a method of treating, inhibiting, ameliorating, or reducing the occurrence of osteoarthritis in a subject in need thereof, or at least one symptom associated with osteoarthritis, comprising administering to the subject a therapeutically effective amount of an antibody or antigen binding fragment thereof in combination with a second therapeutic agent. Examples of a second therapeutic agent having applications in the method of the present invention include, but are not limited to, a second NGF antibody, a non-steroidal anti-inflammatory drug (NSAID), an oral or injectable glucocorticoid, an opioid, tramadol, an alpha-2-delta ligand and hyaluronic acid.

In one embodiment, an antibody or antigen-binding fragment thereof having applications in a method of the present invention is administered as an initial dose of at least approximately about 0.1 mg to about 800 mg. In certain embodiments, an antibody or antigen-binding fragment thereof having applications in a method of the present invention is administered as an initial dose of at least approximately about 5 to about 100 mg. In other embodiments, an antibody or antigen-binding fragment thereof having applications in a method of the present invention is administered as an initial dose of at least approximately about 10 to about 50 mg. In specific embodiments, the initial dose may be followed by administration of a second or a plurality of subsequent doses of the antibody or antigen-binding fragment thereof in an amount that is approximately the same or less than that of the initial dose, wherein the subsequent doses are separated by at least one day; at least one week, at least 2 weeks; at least 3 weeks; at least 4 weeks; at least 5 weeks; at least 6 weeks; at least 7 weeks; at least 8 weeks; at least 9 weeks; at least 10 weeks; at least 12 weeks; or at least 14 weeks.

A particular example of an antibody or antigen-binding fragment thereof having applications in a method of the present invention is mAb1 (HCVR/LCVR SEQ ID NO:24/26).

BRIEF DESCRIPTION OF THE DRAWINGS

FIG. 1 shows the clinical study flowchart.

DETAILED DESCRIPTION

Before the present methods are described, it is to be understood that this invention is not limited to particular methods, and experimental conditions described, as such methods and conditions may vary. It is also to be understood that the terminology used herein is for the purpose of describing particular embodiments only, and is not intended to be limiting, since the scope of the present invention will be defined in and limited only by the appended claims.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, preferred methods and materials are now described. All publications mentioned herein are incorporated herein by reference in their entirety.

Anti-NGF Antibodies and Antigen-Binding Fragments Thereof

The method of the invention relates to the use of an anti-NGF antibody or antibody fragment that specifically binds NGF. The term "human nerve growth factor" or "NGF", as used herein, refers to human NGF having the nucleic acid sequence shown in SEQ ID NO:1 and the amino acid sequence of SEQ ID NO:2, or a biologically active fragment thereof.

The term "specifically binds," means that an antibody or antigen-binding fragment thereof forms a complex with an antigen that is relatively stable under physiologic conditions. Specific binding can be characterized by a equilibrium dissociation constant of about $1 \times 10^{-6}$ M or smaller. Methods for determining whether two molecules specifically bind are well known in the art and include, for example, equilibrium dialysis, surface plasmon resonance, and the like.

An "antibody" is an immunoglobulin molecule comprised of four polypeptide chains, two heavy (H) chains and two light (L) chains inter-connected by disulfide bonds. Each heavy chain is comprised of a heavy chain variable region ("HCVR" or "$V_H$") and a heavy chain constant region ($C_H$) comprised of three domains, $C_H1$, $C_H2$ and $C_H3$. Each light chain is comprised of a light chain variable region ("LCVR or "$V_L$") and a light chain constant region ($C_L$). The light chain constant region is comprised of one domain, $C_L$. The $V_H$ and $V_L$ regions can be further subdivided into regions of hypervariability, termed complementarity determining regions (CDR), interspersed with regions that are more conserved, termed framework regions (FR). Each HCVR and LCVR is composed of three CDRs and four FRs, arranged from amino-terminus to carboxy-terminus in the following order: FR1, CDR1, FR2, CDR2, FR3, CDR3, FR4. In certain embodiments of the invention, the FRs of the anti-NGF antibody (or antigen binding fragment thereof) may be identical to the human germline sequences, or may be naturally or artificially modified. An amino acid consensus sequence may be defined based on a side-by-side analysis of two or more CDRs.

The fully-human anti-NGF antibodies disclosed herein may comprise one or more amino acid substitutions, insertions and/or deletions in the framework and/or CDR regions of the heavy and light chain variable domains as compared to the corresponding germline sequences. Such mutations can be readily ascertained by comparing the amino acid sequences disclosed herein to germline sequences available from, for example, public antibody sequence databases. The present invention includes antibodies, and antigen-binding fragments thereof, which are derived from any of the amino acid sequences disclosed herein, wherein one or more amino acids within one or more framework and/or CDR regions are mutated to the corresponding residue(s) of the germline sequence from which the antibody was derived, or to the corresponding residue(s) of another human germline sequence, or to a conservative amino acid substitution of the corresponding germline residue(s) (such sequence changes are referred to herein collectively as "germline mutations"). A person of ordinary skill in the art, starting with the heavy and light chain variable region sequences disclosed herein, can easily produce numerous antibodies and antigen-binding fragments which comprise one or more individual germline mutations or combinations thereof. In certain embodiments, all of the framework and/or CDR residues within the $V_H$ and/or $V_L$ domains are mutated back to the residues found in the original germline sequence from which the antibody was derived. In other embodiments, only certain residues are mutated back to the original germline sequence, e.g., only the mutated residues found within the first 8 amino acids of FR1 or within the last 8 amino acids of FR4, or only the mutated residues found within CDR1, CDR2 or CDR3. In other embodiments, one or more of the framework and/or CDR residue(s) are mutated to the corresponding residue(s) of a different germline sequence (i.e., a germline sequence that is different from the germline sequence from which the antibody was originally derived). Furthermore, the antibodies of the present invention may contain any combination of two or more germline mutations within the framework and/or CDR regions, e.g., wherein certain individual residues are mutated to the corresponding residue of a particular germline sequence while certain other residues that differ from the original germline sequence are maintained or are mutated to the corresponding residue of a different germline sequence. Once obtained, antibodies and antigen-binding fragments that contain one or more germline mutations can be easily tested for one or more desired property such as, improved binding specificity, increased binding affinity, improved or enhanced antagonistic or agonistic biological properties (as the case may be), reduced immunogenicity, etc. Antibodies and antigen-binding fragments obtained in this general manner are encompassed within the present invention.

The present invention also includes anti-NGF antibodies comprising variants of any of the HCVR, LCVR, and/or CDR amino acid sequences disclosed herein having one or more conservative substitutions. For example, the present invention includes anti-NGF antibodies having HCVR, LCVR, and/or CDR amino acid sequences with, e.g., 20 or fewer, 10 or fewer, 8 or fewer, 6 or fewer, 4 or fewer, etc. conservative amino acid substitutions relative to any of the HCVR, LCVR, and/or CDR amino acid sequences disclosed herein.

The term "antigen-binding fragment" of an antibody (or "antibody-binding portion"), as used herein, refers to one or more fragments of an antibody that retain the ability to specifically bind to an antigen (e.g., NGF). An antibody fragment may include, for example, a Fab fragment, a F(ab')$_2$ fragment, a Fv fragment, a dAb fragment, a fragment containing a CDR, or an isolated CDR.

In certain embodiments, an antibody or antibody fragment of the invention may be conjugated to a therapeutic moiety ("immunoconjugate"), such as a cytotoxin, a chemotherapeutic drug, an immunosuppressant or a radioisotope. A therapeutic moiety that is a cytotoxin includes any agent that is detrimental to cells.

In certain embodiments, the antibody or antibody fragment for use in the method of the invention may be monospecific, bispecific, or multispecific. Multispecific antibodies may be specific for different epitopes of one target polypeptide or may contain antigen-binding domains specific for epitopes of more than one target polypeptide. An exemplary bi-specific antibody format that can be used in the context of the present invention involves the use of a first immunoglobulin (Ig) $C_H3$ domain and a second Ig $C_H3$ domain, wherein the first and second Ig $C_H3$ domains differ from one another by at least one amino acid, and wherein at least one amino acid difference reduces binding of the bispecific antibody to Protein A as compared to a bi-specific antibody lacking the amino acid difference. In one embodiment, the first Ig $C_H3$ domain binds Protein A and the second Ig $C_H3$ domain contains a mutation, such as an H95R modification (by IMGT exon numbering; H435R by EU numbering), which reduces or abolishes Protein A binding. The second $C_H3$ may further comprise an Y96F modification (by IMGT; Y436F by EU). Further modifications that may be found within the second $C_H3$ include: D16E, L18M, N44S, K52N, V57M, and V82I (by IMGT; D356E, L358M, N384S, K392N, V397M, and V422I by EU) in the case of IgG1 antibodies; N44S, K52N, and V82I (IMGT; N384S, K392N, and V422I by EU) in the case of IgG2 antibodies; and Q15R, N44S, K52N, V57M, R69K, E79Q, and V82I (by IMGT; Q355R, N384S, K392N, V397M, R409K, E419Q, and V422I by EU) in the case of IgG4 antibodies. Variations on the bi-specific antibody format described above are contemplated within the scope of the present invention.

Therapeutic Administration and Formulations

The invention provides methods of using therapeutic compositions comprising anti-NGF antibodies or antigen-binding fragments thereof. The therapeutic compositions of the invention will be administered with suitable carriers, excipients, and other agents that are incorporated into formulations to provide improved transfer, delivery, tolerance, and the like. A multitude of appropriate formulations are available to the skilled artisan such as those that can be found in the formulary known to all pharmaceutical chemists: Remington's Pharmaceutical Sciences, Mack Publishing Company, Easton, Pa. These formulations include, for example, powders, pastes, ointments, jellies, waxes, oils, lipids, lipid (cationic or anionic) containing vesicles (such as LIPOFECTIN™), DNA conjugates, anhydrous absorption pastes, oil-in-water and water-in-oil emulsions, emulsions carbowax (polyethylene glycols of various molecular weights), semi-solid gels, and semi-solid mixtures containing carbowax. See also Powell et al. "Compendium of excipients for parenteral formulations" PDA (1998) J Pharm Sci Technol 52:238-311.

The dose may vary depending upon the age and the weight of a subject to be administered, target disease, conditions, route of administration, and the like. When the antibody of the present invention is used for treating various conditions and diseases associated with NGF, including inflammatory pain, neuropathic and/or nociceptive pain, hepatocellular carcinoma, breast cancer, liver cirrhosis, and the like, in an adult patient, it is advantageous to administer the antibody of the present invention either intravenously or subcutaneously, normally at a single dose of about 0.01 to about 20 mg/kg body weight, more preferably about 0.02 to about 7, about 0.03 to about 5, or about 0.05 to about 3 mg/kg body weight. Depending on the severity of the condition, the frequency and the duration of the treatment can be adjusted.

Various delivery systems are known and can be used to administer the pharmaceutical composition of the invention, e.g., encapsulation in liposomes, microparticles, microcapsules, receptor mediated endocytosis (see, e.g., Wu et al. (1987) J. Biol. Chem. 262:4429-4432). Methods of introduction include, but are not limited to, intradermal, intramuscular, intraperitoneal, intravenous, subcutaneous, intranasal, epidural, and oral routes. The composition may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local.

The pharmaceutical composition can also be delivered in a vesicle, in particular a liposome (see Langer (1990) Science 249:1527-1533). In certain situations, the pharmaceutical composition can be delivered in a controlled release system, for example, with the use of a pump or polymeric materials. In another embodiment, a controlled release system can be placed in proximity of the composition's target, thus requiring only a fraction of the systemic dose.

The injectable preparations may include dosage forms for intravenous, subcutaneous, intracutaneous and intramuscular injections, local injection, drip infusions, etc. These injectable preparations may be prepared by methods publicly known. For example, the injectable preparations may be prepared, e.g., by dissolving, suspending or emulsifying the antibody or its salt described above in a sterile aqueous medium or an oily medium conventionally used for injections. As the aqueous medium for injections, there are, for example, physiological saline, an isotonic solution containing glucose and other auxiliary agents, etc., which may be used in combination with an appropriate solubilizing agent such as an alcohol (e.g., ethanol), a polyalcohol (e.g., propylene glycol, polyethylene glycol), a nonionic surfactant [e.g., polysorbate 80, HCO-50 (polyoxyethylene (50 mol) adduct of hydrogenated castor oil)], etc. As the oily medium, there are employed, e.g., sesame oil, soybean oil, etc., which may be used in combination with a solubilizing agent such as benzyl benzoate, benzyl alcohol, etc. The injection thus prepared is preferably filled in an appropriate ampoule.

A pharmaceutical composition of the present invention can be delivered subcutaneously or intravenously with a standard needle and syringe. In addition, with respect to subcutaneous delivery, a pen delivery device readily has applications in delivering a pharmaceutical composition of the present invention. Such a pen delivery device can be reusable or disposable. A reusable pen delivery device generally utilizes a replaceable cartridge that contains a pharmaceutical composition. Once all of the pharmaceutical composition within the cartridge has been administered and the cartridge is empty, the empty cartridge can readily be discarded and replaced with a new cartridge that contains the pharmaceutical composition. The pen delivery device can then be reused. In a disposable pen delivery device, there is no replaceable cartridge. Rather, the disposable pen delivery device comes prefilled with the pharmaceutical composition held in a reservoir within the device. Once the reservoir is emptied of the pharmaceutical composition, the entire device is discarded.

Numerous reusable pen and autoinjector delivery devices have applications in the subcutaneous delivery of a pharmaceutical composition of the present invention. Examples include, but certainly are not limited to AUTOPEN™ (Owen Mumford, Inc., Woodstock, UK), DISETRONIC™ pen (Disetronic Medical Systems, Burghdorf, Switzerland), HUMALOG MIX 75/25™ pen, HUMALOG™ pen, HUMALIN 70/30™ pen (Eli Lilly and Co., Indianapolis, Ind.), NOVOPEN™ I, II and III (Novo Nordisk, Copenhagen, Denmark), NOVOPEN JUNIOR™ (Novo Nordisk, Copenhagen, Denmark), BD™ pen (Becton Dickinson, Franklin Lakes, N.J.), OPTIPEN™ OPTIPEN PRO™, OPTIPEN STARLET™, and OPTICLIK™ (Sanofi-Aventis, Frankfurt, Germany), to name only a few. Examples of disposable pen delivery devices having applications in subcutaneous delivery of a pharmaceutical composition of the present invention include, but certainly are not limited to the SOLOSTAR™ pen (Sanofi-Aventis), the FLEXPEN™ (Novo Nordisk), and the KWIKPEN™ (Eli Lilly), the SURECLICK™ Autoinjector (Amgen, Thousands Oaks, Calif.), the PENLET™ (Haselmeier, Stuttgart, Germany), the EPIPEN (Dey, L. P.) and the HUMIRA™ Pen (Abbott Labs, Abbott Park, Ill.), to name only a few.

Advantageously, the pharmaceutical compositions for oral or parenteral use described above are prepared into dosage forms in a unit dose suited to fit a dose of the active ingredients. Such dosage forms in a unit dose include, for example, tablets, pills, capsules, injections (ampoules, prefilled syringes or auto-injectors), suppositories, etc. The amount of the aforesaid antibody contained is generally about 0.1 to 800 mg per dosage form in a unit dose; especially in the form of injection, it is preferred that the aforesaid antibody is contained in about 1 to 250 mg or about 10 to 100 mg for the other dosage forms.

By the phrase "therapeutically effective amount" is meant an amount that produces the desired effect for which it is administered. The exact amount will depend on the purpose of the treatment, and will be ascertainable by one skilled in the art using known techniques (see, for example, Lloyd (1999) The Art, Science and Technology of Pharmaceutical Compounding).

In specific embodiments of the therapeutic methods of the invention, a subject suffering from osteoarthritis may be treated with a combination of an antibody or antibody fragment of the invention and optionally with at least a second therapeutic agent. Examples of a second therapeutic agent having applications in a method of the present invention include, but are not limited to, a non-steroidal anti-inflammatory drug (NSAID), an oral or injectable glucocorticoid, an opioid, tramadol, an alpha-2-delta ligand or hyaluronic acid.

EXAMPLES

The following examples are put forth so as to further provide those of ordinary skill in the art with a complete disclosure and description of how to make and use the methods and compositions of the invention, and are not intended to limit the scope of what the inventors regard as their invention. Efforts have been made to ensure accuracy with respect to numbers used (e.g., amounts, temperature, etc.) but some experimental errors and deviations should be understood. Unless indicated otherwise, parts are parts by weight, molecular weight is average molecular weight, temperature is in degrees Centigrade, and pressure is at or near atmospheric. The statistical analyses were conducted according to mixed Factorial ANOVA with Bondferroni post hoc or Tukey HSD post hoc tests.

Example 1. Study of Anti-NGF Antibody in Patients with Osteoarthritis of the Knee A double-blind study in which patients with osteoarthritis (OA) of the knee are randomized to 1 of 4 treatment arms (3 active and 1 placebo) was conducted. Randomization was stratified by Baseline walking knee pain score (>7 and ≤7). Each patient received a dose of a fully human anti-NGF mAb (mAb1) or placebo at baseline (Day 1) and at week 8 (Day 57) for a total of 2 doses.

The doses evaluated were 0.03, 0.1, or 0.3 mg/kg administered intravenously (IV). Approximately 53 patients were enrolled in each treatment arm.

Patients of the target population were asked to discontinue their current pain medications prior to the baseline visit and for the duration of the study (end of week 24 [Day 169]). Rescue medication (acetaminophen) was allowed during this time (a maximum of 4 g per day, but not for more than 4 consecutive days). Low-dose aspirin (up to 325 mg/day) was also allowed. The duration of the washout period prior to baseline (Day 1) was determined by the half-life of the medication (approximately 5 half-lives).

Patients received study drug on Day 1 (baseline) and at week 8 (Day 57). Patients were followed for 16 weeks after the second infusion, until the end of week 24 (Day 169), for a total study duration of 24 weeks for each patient.

Safety and tolerability of mAb1 was assessed by evaluating the incidence of treatment-emergent adverse events (TEAEs) from Day 1 to the end of week 24 (Day 169) or study withdrawal, by patient medical history, physical examination, monitoring of vital signs and ECGs, clinical laboratory testing, and neurological assessments of sensory (tactile, pain, and vibration) and motor (muscle strength, and reflex) function.

The effect of mAb1 on walking knee pain was assessed using the numerical rating scale (NRS). Patients were asked to report the average intensity of their walking knee pain daily for the duration of the 24-week study. Changes in OA status were assessed using the WOMAC (pain, stiffness and function subscales). The patient's assessment of overall treatment effect was assessed by the Patient Global Impression of Change (PGIC). The patient's assessment of quality of life (QOL) was assessed using the SF-12 Scale.

Serum samples were collected for PK analysis, anti-mAb1 antibody evaluation, and exploratory proteomic and gene expression (RNA) analysis.

Patients completed the study when they received 2 doses of mAb1 or placebo and completed all scheduled safety and efficacy assessments to week 24 (Day 169).

Target Population. Eligible patients for this study were men and women between 40 and 75 years of age, with a diagnosis of OA of the knee and who have experienced moderate to severe knee pain for an average period of ≥3 months.

Inclusion Criteria. A patient met the following criteria, to be eligible for inclusion in the study: (1) Men and women ≥40 and ≤75 years of age; (2) Diagnosis of OA of the knee according to American College of Rheumatology (ACR) criteria, and experiencing moderate to severe pain in the index knee for at least 3 months prior to the screening visit; (3) Kellgren-Lawrence grade 2-3 radiographic severity of the index knee at or within 6 months prior to Screening; (4) No new chronic medications introduced within the past 30 days. This criterion does not apply to the use of acetaminophen as rescue medication; (5) Walking knee pain levels at Screening and Baseline ≥4 on the NRS; (6) Willingness to discontinue currently used pain medications (for 5 half-lives) prior to the baseline visit and throughout the study; (7) Body weight<110 kg; (8) Willing, and able to return for all clinic visits and complete all study-related procedures; (9) Able to read and understand and willing to sign the informed consent form; (10) Able to read, understand, and complete study-related questionnaires.

Exclusion Criteria. A patient who met any of the following criteria was excluded from the study: (1) Significant concomitant illness including, but not limited to, cardiac, renal, neurological, endocrinological, metabolic or lymphatic disease that would adversely affect the patient's participation in the study; (2) Patients with joint replacement in the affected knee; (3) Patients with peripheral neuropathy due to any reason; (4) Known Human Immunodeficiency Virus (HIV) antibody, Hepatitis B surface antigen (HBsAg), and/or Hepatitis C antibody (HCV) at the screening visit by history or testing; (5) Known sensitivity to doxycycline or mAb therapeutics; (6) Other medical or psychiatric conditions that could, in the opinion of the Investigator or Sponsor, compromise protocol participation; (7) Participation in any clinical research study evaluating another investigational drug or therapy within 3 weeks or at least 5 half-lives, whichever was longer, of the investigational drug, prior to the screening visit; (8) Previous exposure to an anti-NGF antibody; (9) Women who are pregnant or nursing; (10) Sexually active men or women of childbearing potential who were unwilling to practice adequate contraception during the study (adequate contraceptive measures included stable use of oral contraceptives or other prescription pharmaceutical contraceptives for 2 or more cycles prior to screening; intrauterine device [IUD]; bilateral tubal ligation; vasectomy; condom or diaphragm plus either contraceptive sponge, foam or jelly); (11) Women of childbearing potential who had either a positive serum pregnancy test result at screening or a positive urine pregnancy test result at baseline. (Women had to be amenorrheic for at least 12 months in order to be considered post-menopausal); (12) Current or prior substance abuse, alcohol abuse, or abuse of prescription pain medication.

Investigational Treatment. Sterile mAb1 Drug Product 20 mg/ml was provided in an aqueous buffered vehicle, pH 5.0, containing 10 mM acetate, 20% (w/v) sucrose and 1% (w/v) PEG 3500. Drug was supplied in a 5 ml glass vial.

Reference Treatment. Placebo was supplied in matched vials containing the same volume of aqueous buffered vehicle (pH 5.0), but with no active protein.

Dose Administration and Schedule. Study drug (mA1 or placebo) was administered on baseline (Day 1) and at week 8 (Day 57). Prior to IV administration, the pharmacist or designee withdrew the required amount of study drug (depending on the patient's dose and weight) from a single-use vial and injected it into an infusion bag of normal saline for infusion. Calculations to determine the volume to be withdrawn were provided in the Site Study Manual.

Method of Treatment Assignment. Randomization was in a 1:1:1:1 ratio between the 4 treatment arms. On Day 1, patients were randomized to receive either mAb1 at a dose of 0.03 mg/kg, 0.1 mg/kg, 0.3 mg/kg, or placebo (in a 1:1:1:1 ratio) according to a pre-determined central randomization scheme. Randomization was stratified by baseline walking knee pain scores (>7 and ≤7).

Data Collection. Study assessments and procedures are shown in the Study Flowchart (FIG. 1). For early termination patients, all week 24 (End-of-study) assessments were performed when the patient returned to the clinic for the final visit. All visits after Day 1 were scheduled within a ±2-day window. X-Ray of knee affected with OA (semi-flexed) was taken only if existing film was not available within 6 months of screening date. At baseline (Day 1) and on Day 57, vital signs were measured immediately prior to dosing, at 15-minute intervals during the infusion, at the end of the infusion, and 1, 2, and 4 hours after the completion of the infusion. Average walking knee pain was assessed at all clinic visits using the NRS. In-between visits, patients were asked to report the average intensity of their walking knee pain DAILY via the IVRS. On Day 1 and week 8 (Day 57), samples were collected prior to the start of the infusion, immediately post-infusion, and at 1, 2, and 4 hours post-infusion.

Visit Descriptions. Screening/Day −14 to −3: Informed consent was obtained before performing or initiating any study-related procedures. The following information was collected: Inclusion/exclusion criteria; Demographics; Medical history and concurrent illnesses including any pre-dose symptoms or ongoing AEs; Concomitant medications; The following procedures and assessments were conducted: X-Ray of knee affected with OA (semi-flexed) which was taken only if an existing film was not available within 6 months prior to screening; Physical examination; Vital signs, height and weight; ECG; Serum pregnancy test for women of childbearing potential; Hematology; Serum Chemistry; Urinalysis. After screening was completed and a patient was deemed eligible to participate, a discussion was held with the patient to discuss the need to stop their current analgesic medications for a specified number of days prior to the baseline visit. The duration of this washout period was based upon the half-life of the medication(s). In addition, patients were told that they must remain off their medications for the duration of the study.

Treatment Period. Baseline/Day 1: At this visit subjects were randomized to a study treatment and received either study drug or placebo. The following information was collected prior to the administration of study drug: Concomitant medications; Presence of any AEs; The following procedures and assessments were conducted prior to the administration of study drug: Vital signs (measured immediately prior to dosing, at 15-minute intervals during the infusion, at the end of the infusion, and 1, 2, and 4 hours post infusion); Urine pregnancy test for women of childbearing potential; Hematology; Serum Chemistry; Urinalysis; Neurological evaluation; Walking knee pain; WOMAC; QOL Questionnaire; Blood sample collection for PK analysis (samples were collected prior to infusion, immediately post-infusion, and at 1, 2 and 4 hours post infusion); Blood sample for anti-mAb1 antibody assessment; Blood sample for exploratory proteomic and gene expression (RNA) analysis; Instruction in use of IVRS.

Week 1/Day 8 (±2 Days). The following information was collected: Concomitant medications; Presence of any AEs. The following procedures and assessments were conducted: Vital signs; Neurological evaluation; Walking knee pain; WOMAC; Patient Global Impression of Change; Blood sample collection for PK analysis; Blood sample for exploratory proteomic and gene expression (RNA) analysis; Review of compliance with IVRS.

Week 2/Day 15 (±2 Days). The following information was collected: Concomitant medications; Presence of any AEs. The following procedures and assessments were completed: Vital signs; Neurological Evaluation; Walking knee pain; WOMAC; Blood sample collection for PK analysis; Review of compliance with IVRS.

Week 4/Day 29 (±2 Days). The following information was collected: Concomitant medications; Presence of any AEs. The following procedures and assessments were conducted: Vital signs; Hematology; Serum Chemistry; Urinalysis; Neurological evaluation; Walking knee pain; WOMAC; Patient Global Impression of Change; QOL Questionnaire; Blood sample collection for PK analysis; Blood sample for exploratory proteomic and gene expression (RNA) analysis; Review of compliance with IVRS.

Week 8/Day 57 (±2 Days). Patients received the second dose of study drug on Day 57. Prior to receiving study drug, the following information was collected: Concomitant medications; Presence of any AEs; The following procedures and assessments were also conducted prior to the administration of study drug: Physical examination; Vital signs and weight (vital signs measured immediately prior to dosing, at 15-minute intervals during the infusion, at the end of the infusion, and 1, 2, and 4 hours post infusion); ECG; Urine pregnancy test for women of childbearing potential; Hematology; Serum Chemistry; Urinalysis; Neurological evaluation; Walking knee pain; WOMAC; Patient Global Impression of Change; QOL Questionnaire; Blood sample collection for PK analysis (samples were collected prior to infusion, immediately post-infusion, and at 1, 2 and 4 hours post infusion); Blood sample for mAb1 antibody assessment; Blood sample for exploratory proteomic and gene expression (RNA) analysis; Review of compliance with IVRS.

Week 10/Day 71 (±2 Days). The following information was collected: Concomitant medications; Presence of any AEs. The following procedures and assessments were conducted: Vital signs; Neurological evaluation; Walking knee pain; WOMAC; Blood sample collection for PK analysis; Review of compliance with IVRS.

Week 12/Day 85 (±2 Days). The following information was collected: Concomitant medications; Presence of any AEs. The following procedures and assessments were conducted: Vital signs; Hematology; Serum Chemistry; Urinalysis; Neurological valuation; Walking knee pain; WOMAC; Patient Global Impression of Change; QOL Questionnaire; Blood sample collection for PK analysis; Blood sample for mAb1 antibody assessment; Blood sample for exploratory proteomic and gene expression (RNA) analysis; Review of compliance with IVRS. Week 16/Day 113 (±2 days). The following information was collected: Concomitant medications; Presence of any AEs. The following procedures and assessments were conducted: Vital signs; Hematology; Serum Chemistry; Urinalysis; Neurological evaluation; Walking knee pain; WOMAC; Patient Global Impression of Change; QOL Questionnaire; Blood sample collection for PK analysis; Review of compliance with IVRS.

Week 20/Day 141 (±2 Days). The following information was collected: Concomitant medications; Presence of any AEs. The following procedures and assessments were conducted: Vital signs; Hematology; Serum Chemistry; Urinalysis; Neurological evaluation; Walking knee pain; WOMAC; Patient Global Impression of Change; QOL Questionnaire; Blood sample collection for PK analysis; Review of compliance with IVRS.

End of Study Assessments (Week 24/Day 169) (±2 Days). The following information was collected during the end-of-study visit: Concomitant medications; Presence of any AEs. The following procedures and assessments were conducted: Physical examination; Vital signs and weight; ECG; Urine pregnancy test for women of childbearing potential; Hematology; Serum Chemistry; Urinalysis; Neurological evaluation; Walking knee pain; WOMAC; Patient Global Impression of Change; QOL Questionnaire; Blood sample collection for PK analysis; Blood sample for anti-mAb1 antibody assessment; Blood sample for exploratory proteomic and gene expression (RNA) analysis; Review of compliance with IVRS.

Walking Knee Pain. The key efficacy endpoint in this study was the mean change from baseline in walking knee pain using the NRS at each study visit until Week 24. The baseline value was defined as the NRS value from Visit 2 and the weekly NRS value up to Week 24 (End of Study [EOS]) were defined as the average of daily assessments measured during the week. Patients reviewed the intensity of their knee pain with the appropriate study site personnel during their scheduled clinic visits and this information was recorded in the eCRF. Patients were also asked to record the average intensity of their walking knee pain daily, using the IVRS system, during their participation in the study. Daily assessment and recording of walking knee pain was performed at the same time each day when possible. The Numerical Rating Scale (NRS) instructed the patient to rate their pain on a 0-10 pain rating scale, 0 means no pain and 10 means the worst possible pain. The middle of the scale (around 5) was considered to be moderate pain. A value of 2 or 3 was considered to be mild pain, but a value of 7 or higher was considered to be severe pain.

Western Ontario and McMaster Osteoarthritis Index (WOMAC). The WOMAC Index was used to assess patients with OA of the hip or knee using 24 parameters in three areas: pain (5 items), stiffness (2 items), and function (17 items). It can be used to monitor the course of a disease or to determine effectiveness of medications. Patients completed the WOMAC (pain, stiffness and function subscales) at baseline (Day 1), week 1 (Day 8), week 2 (Day 15), week 4 (Day 29), week 8 (Day 57), week 10 (Day 71), week 12 (Day 85), week 16 (Day 113), week 20 (Day 141), and at the end-of-study (week 24 [Day 169]). Patients were asked to score each of the 24 parameters using the scale shown in Table 1. The patient was asked to rate each statement on a Likert item, ranging from 0 (none) to 10 (extreme). Pain dimension subscale was calculated as the average score of Q1 to Q5 (Thumboo et al (2001), Osteoarthritis Cartilage, July; 9(5):440-6.). Stiffness dimension subscale was calculated as the average score of Q6 and Q7. Function dimension subscale was calculated as the average score of Q8 to Q24. Standardized total scale will be calculated as the average score from all 24 questions. Change from baseline in the above subscales and the standardized total scale to each measurement visit was analyzed.

TABLE 1

| Response | Points |
| --- | --- |
| none | 0 |
| slight | 1 |
| moderate | 2 |
| severe | 3 |
| extreme | 4 |

WOMAC parameters: Pain: 1. Walking on a flat surface; 2. Stair climbing; 3. Nocturnal (at night, lying in bed); 4. Rest (sitting or lying down); 5. Weight bearing (standing upright). Stiffness: 6. Morning stiffness; 7. Stiffness occurring later in the day. Function: 8. Difficulty descending stairs; 9. Difficulty ascending stairs; 10. Rising from sitting; 11. Standing; 12. Bending to floor (to pick something up); 13. Walking on a flat surface; 14. Getting in or out of car; 15. Going shopping; 16. Putting on socks; 17. Rising from bed; 18. Taking off socks; 19. Lying in bed; 20. Getting in and out of the bathtub; 21. Difficulty sitting (for a period of time); 22. Getting on or off toilet; 23. Heavy domestic duties; 24. Light domestic duties.

Patient Global Impression of Change (PGIC). The PGIC is a patient-rated assessment of response to treatment on a 7-point Likert scale and was completed at week 1 (Day 8), week 4 (Day 29), week 8 (Day 57), week 12 (Day 85), week 16 (Day 113), week 20 (Day 141), and at the end-of-study (week 24 [Day 169]). The recall period for this scale was 1 week. The patient responded to the question "Compared to a week ago, how would you rate your overall status?" by selecting an option from 1. Very Much Improved; 2. Much Improved; 3. Minimally Improved; 4. No Change; 5. Minimally Worse; 6. Much Worse; 7. Very Much Worse.

Quality of Life Questionnaire. The SF-12 is a patient-rated, 12-question assessment of QOL. It is a validated, shorter version of the commonly used SF-36. Both scales assess important QOL domains relevant to patients suffering from a wide range of medical conditions. The SF-12 was completed at week 1 (Day 8), week 4 (Day 29), week 8 (Day 57), week 12 (Day 85), week 16 (Day 113), week 20 (Day 141), and at the end-of-study (week 24 [Day 169]). QOL: A. In general, would you say your health is: Excellent (1), Very Good (2), Good (3), Fair (4), Poor (5). B. Does your health now limit you in these activities? If so, how much? C. Moderate Activities, such as moving a table, pushing a vacuum cleaner, bowling, or playing golf: Yes, Limited A Lot (1), Yes, Limited A Little (2), No, Not Limited At All (3). 3. Climbing several flights of stairs: Yes, Limited A Lot (1), Yes, Limited A Little (2), No, Not Limited At All (3). D. During the past 4 weeks have you had any of the following problems with your work or other regular activities as a result of your physical health? 4. Accomplished less than you would like: Yes (1), No (2). 5. Were limited in the kind of work or other activities: Yes (1), No (2). E. During the past 4 weeks, were you limited in the kind of work you do or other regular activities as a result of any emotional problems (such as feeling depressed or anxious)? 6. Accomplished less than you would like: Yes (1), No (2). 7. Didn't do work or other activities as carefully as usual: Yes (1), No (2). 8. During the past 4 weeks, how much did pain interfere with your normal work (including both work outside the home and housework)? Not At All (1). A Little Bit (2), Moderately (3), Quite A Bit (4), Extremely (5). F. The next three questions are about how you feel and how things have been during the past 4 weeks. For each question, please give the one answer that comes closest to the way you have been feeling. How much of the time during the past 4 weeks—9. Have you felt calm and peaceful? All of the Time (1), Most of the Time (2), A Good Bit of the Time (3), Some of the Time (4), A Little of the Time (5), None of the Time (6). 10. Did you have a lot of energy? All of the Time (1), Most of the Time (2), A Good Bit of the Time (3), Some of the Time (4), A Little of the Time (5), None of the Time (6). 11. Have you felt downhearted and blue? All of the Time (1), Most of the Time (2), A Good Bit of the Time (3), Some of the Time (4), A Little of the Time (5), None of the Time (6). 12. During the 4 weeks, how much of the time has your physical health or emotional problems interfered with your social activities (like visiting with friends, relatives, etc.)? All of the Time (1), Most of the Time (2), A Good Bit of the Time (3), Some of the Time (4), A Little of the Time (5), None of the Time (6). This questionnaire yields an 8-scale profile of functional health and well-being scores as well as psychometrically based physical and mental health summary measures which are physical component summary (PCS) and mental component summary (MCS), respectively. Change from baseline in the standardized summary scores (MCS and PCS) to each measurement visit was analyzed.

Neurological Evaluation. 1. Evaluation of Sensory function: A neurological evaluation of sensory function assesses tactile sense (light touch), pain sensation (pin prick or other) and vibration sense (tuning fork). 2. Evaluation of Motor function: A neurological evaluation of motor function assesses muscle strength (movement of upper and lower limbs against resistance) and reflexes (upper and lower limbs e.g., tricep and patellar tendons). If changes in sensation or motor function were observed or elicited during the study, they were monitored closely by the Investigator. If these changes became persistent, evolved or became severe in intensity, the Investigator referred the patient to a neurologist for a more comprehensive diagnostic evaluation. 3. Persistence of symptoms: For the purpose of this protocol, "persistence" of sensory or motor symptoms was defined as "lasting for a period of 2 weeks and with no improvement in severity." Persistence of symptoms for 2 weeks or longer triggered an examination of the patient and a referral for neurological consultation, if deemed appropriate. In addition, the Investigator referred any patient at any time for a neurologic consultation if felt to be clinically indicated. 4. Evolution of symptoms: Evolution of symptoms in any timeframe triggered a neurological examination. For example, if a sensory change of "numbness" or "pins and needles" evolved into more dysesthestic or allodynic sensations such as "burning" or "painful", it did not matter when it occurred during the course of the study or how long it took for the change to occur. Any patient who experienced such a change was referred for a thorough neurological assessment whenever a change like this was reported. In addition, as noted above, the Investigator referred any patient for a neurologic consultation at any time, if it was felt to be clinically indicated. Clinical neurological assessments of sensory and motor function were conducted at baseline (Day 1), and at week 1 (Day 8), week 2 (Day 15), week 4 (Day 29), week 8 (Day 57), week 10 (Day 71), week 12 (Day 85), week 16 (Day 113), week 20 (Day 141), and at the end-of-study (week 24 [Day 169]).

Pharmacokinetic and Antibody Sample Collection. Drug Concentration Measurements and Samples. Serum samples for PK measurements were collected at every study visit beginning at baseline (Day 1), and at week 1 (Day 8), week 2 (Day 15), week 4 (Day 29), week 8 (Day 57), week 10 (Day 71), week 12 (Day 85), week 16 (Day 113), week 20 (Day 141), and at the end of study visit (week 24/Day 169). On study treatment days (Day 1 and week 8 [Day 57]), samples were collected prior to the start of the infusion, immediately post infusion, and at 1, 2, and 4 hours post-infusion.

Antibody Measurements and Samples. Serum samples were collected for analysis of antibodies to mAb1 prior to dosing at baseline (Day 1), after administration of the second dose (week 8 [Day 57]), at week 12 (Day 85), and at the end of study (week 24 [Day 169]).

Use and Storage of Exploratory Serum and RNA Samples. Exploratory samples were collected to study NGF, mAb1, pain, OA and inflammation. Ribonucleic acid samples were collected for exploratory microarray expression profiling. All samples were coded to maintain patient confidentiality. Remaining RNA samples after profiling were stored for future analyses.

Serum samples were stored and may be used for future proteomics analyses.

Analysis of Efficacy Data

Key Efficacy Endpoint: Walking Knee Pain

Mean weekly change in NRS of walking knee pain from baseline was analyzed using a mixed-effect model repeated measure (MMRM) approach. The MMRM analyses was implemented via PROC MIXED in SAS by fitting changes from baseline at all post randomization visits in the treatment period up to Week 24.

The statistical inference on the primary efficacy variable, mean change from baseline to Week 24 in pain intensity was derived from this model using an appropriate contrast.

The model included factors (fixed effects) for treatment, baseline-NRS stratum (>7 and ≤7), visit, treatment-by-visit interaction, and baseline value as a covariate. The factor visit with nominal visits has 24 levels (e.g., Week 1 to Week 24).

An unstructured correlation matrix was used to model the within-patient errors. Parameters were estimated using restricted maximum likelihood method with the Newton-Raphson algorithm. Denominator degrees of freedom were estimated using Satterthwaite's approximation. Least squares means (LS-means) estimates at each week by treatment group are provided, as well as the differences of these estimates versus placebo, with their corresponding standard errors and associated 95% confidence intervals. Student t-tests were used to determine the statistical significance of the comparison of each mAb1 dose versus placebo. In addition, data and change from baseline were summarized by treatment group using descriptive statistics (mean, median, standard deviation, minimum and maximum) by visits based on Observed Cases (OC). Graphical presentations will be used to illustrate trends over time.

If the algorithm does not converge or any other computational issue occurs, the mean weekly change in NRS of walking knee pain from baseline was analyzed using an Analysis of Covariance (ANCOVA) approach. The ANCOVA analyses was implemented via PROC Mixed in SAS by fitting changes from baseline at all post randomization visits in the treatment period up to Week 24. In the event that the mixed model assumptions did hold, rank-based ANCOVA was performed. In the event that the ANCOVA assumptions did not hold, rank-based ANCOVA was performed.

The mean weekly NRS was calculated as the average of the reported daily NRS within the week (prorated mean). If the mean weekly change in NRS of walking knee pain from baseline for a specific week was missing, the MMRM handled missing data by incorporating all available data at any weekly time points for each patient into the analysis and utilizing all existing correlations between the weekly time points. For the ANCOVA approach, the last existing value prior to this week was used (Last Observation Carried Forward [LOCF] procedure).

Proportions of patients with 30% or more reduction (30% responder rate) and 50% responder rate from baseline at each week were summarized and plotted by the treatment group. Fisher's exact test was applied to compare each treatment group with placebo group.

Other Efficacy Endpoints
WOMAC Index

Change from baseline in 3 subscales (pain, stiffness and function) and the standardized total scale to each measurement visit was analyzed similarly as for the key efficacy variable.

In the MMRM or ANCOVA model, the factor visit with nominal visits has 9 levels (e.g., Week 1, Week 2, Week 4, Week 8, Week 10, Week 12, Week 16, Week 20 and Week 24).

Dimension scores were computed if at least 50% of items were available within the corresponding dimension. LOCF procedure was used for the missing data imputation for ANCOVA approach.

PGIC

PGIC at each measurement visit, as a multinomial repeated measure with 7 categories, was analyzed as for the key efficacy variable. The model excluded the baseline and the factor visit with nominal visits had 7 levels (e.g., Week 1, Week 4, Week 8, Week 12, Week 16, Week 20 and Week 24). Due to the nature of non-normality, Minimum Variance Quadratic Unbiased Estimation (MIVQUE) method was specified in the SAS Proc Mixed to estimate the covariance parameters.

If the algorithm did not converge or any other computational issue occurred, an analysis of variance (ANOVA) model was applied. The ANOVA analyses were implemented via PROC Mixed in SAS at all post randomization visits in the treatment period up to Week 24. In the event that the ANOVA assumptions did not hold, rank-based ANOVA was performed.

LOCF procedure was used for the missing data imputation for the ANOVA approach.

Quality of Life Questionnaire (SF-12)

Change from baseline in the standardized summary scores (MCS and PCS) to each measurement visit were analyzed similarly as for the key efficacy variable.

In MMRM or ANCOVA model, the factor visit with nominal visits had 6 levels (e.g., Week 4, Week 8, Week 12, Week 16, Week 20 and Week 24).

Total scores were computed if at least 50% of items were available. The missing items were imputed by the mean of available items. Dimension scores were computed if at least 50% of items were available within the corresponding dimension.

LOCF procedure was used for the missing data imputation in the ANCOVA approach.

Results
Key Efficacy Endpoint: Walking Knee Pain Assessed Using the Numerical Rating Scale (NRS)

The effect of mAb1 on walking knee pain was assessed using the NRS, as described above.

The results of this landmark analysis, which are summarized in Table 2, indicate that mAb1 provided clinically relevant pain relief for Walking Knee Pain compared to placebo at both the Week 8 and Week 16 evaluations. The effect at Week 24 (16 weeks after the second dose administration) was diminished compared to the earlier timepoints. At Week 8, the 0.1 and 0.3 mg/kg doses were statistically significantly different from placebo at the 5% significance level in the change from baseline. At Week 16, the two lower doses were statistically different from placebo (0.03 and 0.1 mg/kg). None of the doses evaluated were statistically different from placebo at the Week 24 evaluation. As this exploratory timepoint was 16 weeks after the final dose administration, this loss of effect was consistent with the plasma elimination half-life of the drug

TABLE 2

NRS of Walking Knee Pain from Baseline to Week 8, 16 and 24 ---Observed Data Using MMRM (Full Analysis Set)

| Week | Placebo (N = 55) | mAb1 (0.03 mg/kg) (N = 53) | mAb1 (0.1 mg/kg) (N = 53) | mAb1 (0.3 mg/kg) (N = 54) |
|---|---|---|---|---|
| Baseline | | | | |
| N | 55 | 53 | 53 | 54 |
| Mean (SD) | 6.4 (1.69) | 6.6 (1.65) | 6.5 (1.53) | 6.6 (1.47) |
| Median | 6.0 | 7.0 | 7.0 | 7.0 |
| Min:Max | 4:10 | 4:10 | 4:10 | 4:9 |
| Week 8 Original NRS | | | | |
| N | 53 | 50 | 51 | 50 |
| Mean (SD) | 4.3 (2.23) | 3.9 (2.34) | 3.2 (2.22) | 3.1 (2.32) |
| Median | 4.3 | 3.8 | 3.7 | 2.4 |
| Min:Max | 0:8 | 0:9 | 0:8 | 0:9 |
| Change from baseline | | | | |
| N | 53 | 50 | 51 | 50 |
| Mean (SD) | −2.1 (2.08) | −2.8 (2.29) | −3.3 (2.61) | −3.6 (2.48) |
| Median | −2.3 | −2.6 | −3.0 | −3.9 |
| Min:Max | −6:2 | −9:2 | −9:1 | −8:2 |

TABLE 2-continued

NRS of Walking Knee Pain from Baseline to Week 8, 16 and 24 ---Observed Data Using MMRM (Full Analysis Set)

| | | | | |
|---|---|---|---|---|
| Difference vs. placebo [1] | | | | |
| LS Means (SE) | | −0.7 (0.43) | −1.2 (0.42) | −1.3 (0.43) |
| 95% CI | | −1.5:0.1 | −2.0:−0.4 | −2.1:−0.4 |
| P-value | | 0.0981 | 0.0053 | 0.0035 |
| Week 16 | | | | |
| Original NRS | | | | |
| N | 45 | 48 | 45 | 42 |
| Mean (SD) | 3.8 (2.34) | 3.2 (2.08) | 3.1 (2.38) | 3.2 (2.69) |
| Median | 4.1 | 3.2 | 3.0 | 2.9 |
| Min:Max | 0:10 | 0:7 | 0:8 | 0:9 |
| Change from baseline | | | | |
| N | 45 | 48 | 45 | 42 |
| Mean (SD) | −2.5 (2.15) | −3.4 (2.24) | −3.4 (2.58) | −3.3 (2.55) |
| Median | −2.3 | −3.1 | −3.6 | −3.4 |
| Min:Max | −7:2 | −8:2 | −8:2 | −8:2 |
| Difference vs. placebo [1] | | | | |
| LS Means (SE) | | −1.1 (0.46) | −1.0 (0.46) | −0.9 (0.47) |
| 95% CI | | −2.0:−0.1 | −1.9:−0.1 | −1.8:0.0 |
| P-value | | 0.0229 | 0.0267 | 0.0631 |
| Week 24 | | | | |
| Original NRS | | | | |
| N | 33 | 39 | 39 | 35 |
| Mean (SD) | 3.7 (2.44) | 4.1 (2.42) | 3.2 (2.04) | 3.7 (2.70) |
| Median | 4.0 | 4.0 | 3.0 | 4.0 |
| Min:Max | 0:8 | 0:9 | 0:8 | 0:8 |
| Change from baseline | | | | |
| N | 33 | 39 | 39 | 35 |
| Mean (SD) | −2.4 (2.24) | −2.5 (2.23) | −3.3 (2.09) | −2.8 (2.76) |
| Median | −2.7 | −2.2 | −3.0 | −3.0 |
| Min:Max | −8:2 | −7:1 | −8:1 | −8:3 |
| Difference vs. placebo [1] | | | | |
| LS Means (SE) | | −0.1 (0.49) | −0.8 (0.49) | −0.5 (0.50) |
| 95% CI | | −1.1:0.8 | −1.8:0.1 | −1.5:0.4 |
| P-value | | 0.7736 | 0.0894 | 0.2804 |

| Model Effects | P-Value |
|---|---|
| Treatment | 0.0337 |
| Baseline | 0.0015 |
| Time | <0.0001 |
| Time-by-Treatment | <0.0001 |
| Baseline NRS Stratum | 0.0120 |

Note:
SD = standard deviation, CI = confidence interval, SE = standard error.
[1] The difference between each mAb1 treatment group and placebo in term of change from baseline.

Other Efficacy Endpoints
WOMAC Pain Subscale and Function Subscale

The WOMAC Index was used to assess patients with OA of the hip or knee using 24 parameters in three areas: pain (5 items), stiffness (2 items), and function (17 items).

The results of these analyses are summarized in Table 3 (Pain Subsale) and Table 4 (Function Subscale).

As shown in Table 3, the baseline mean WOMAC Pain Subscale scores ranged from 5.7 to 6.4 with the mean score in the patient group given mAb1 at 0.03 mg/kg being the smallest. Treatment effect in terms of the LS mean difference vs. placebo in the group given 0.03 mg/kg of mAb1 was the smallest. For the groups given 0.1 mg/kg and 0.3 mg/kg of mAb1, the LS mean differences vs. placebo were similar and ranged from −0.7 to −1.4. The p-values indicate that the results were statistically significant at Week 8 and Week 16, but not at Week 24.

TABLE 3

WOMAC Pain Subscale from Baseline to Week 8, 16 and 24--- Observed Data Using MMRM (Full Analysis Set)

| Week | Placebo (N = 55) | mAb1 (0.03 mg/kg) (N = 53) | mAb1 (0.1 mg/kg) (N = 53) | mAb1 (0.3 mg/kg) (N = 54) |
|---|---|---|---|---|
| Baseline | | | | |
| N | 55 | 52 | 53 | 54 |
| Mean (SD) | 5.9 (1.79) | 5.7 (1.77) | 6.1 (1.75) | 6.4 (1.97) |
| Median | 6.2 | 5.5 | 6.2 | 6.8 |
| Min:Max | 1:9 | 2:10 | 2:9 | 3:10 |
| Week 8 | | | | |
| Original WOMAC pain subscale | | | | |
| N | 51 | 50 | 50 | 46 |
| Mean (SD) | 4.0 (1.90) | 3.1 (2.05) | 2.7 (2.10) | 2.6 (2.33) |
| Median | 4.0 | 2.8 | 2.3 | 2.1 |
| Min:Max | 0:8 | 0:9 | 0:7 | 0:7 |
| Change from baseline | | | | |
| N | 51 | 49 | 50 | 46 |
| Mean (SD) | −1.9 (1.74) | −2.6 (2.01) | −3.4 (2.54) | −3.5 (2.42) |
| Median | −1.4 | −2.6 | −3.1 | −3.3 |
| Min:Max | −7:2 | −7:3 | −8:1 | −9:3 |
| Difference vs. placebo [1] | | | | |
| LS Means (SE) | | −0.9 (0.39) | −1.4 (0.39) | −1.3 (0.39) |
| 95% CI | | −1.7:−0.1 | −2.2:−0.7 | −2.1:−0.5 |
| P-value | | 0.0228 | 0.0003 | 0.0010 |
| Week 16 | | | | |
| Original WOMAC pain subscale | | | | |
| N | 44 | 47 | 44 | 41 |
| Mean (SD) | 3.5 (2.31) | 2.9 (2.15) | 2.6 (2.15) | 2.8 (2.38) |
| Median | 3.6 | 2.4 | 2.3 | 2.4 |
| Min:Max | 0:10 | 0:10 | 0:8 | 0:8 |
| Change from baseline | | | | |
| N | 44 | 47 | 44 | 41 |
| Mean (SD) | −2.4 (2.18) | −2.7 (1.89) | −3.4 (2.53) | −3.2 (2.24) |
| Median | −1.9 | −2.4 | −3.4 | −3.4 |
| Min:Max | −8:1 | −7:1 | −8:2 | −9:2 |
| Difference vs. placebo [1] | | | | |
| LS Means (SE) | | −0.6 (0.42) | −1.1 (0.42) | −0.8 (0.42) |
| 95% CI | | −1.4:0.2 | −1.9:−0.3 | −1.7:−0.0 |
| P-value | | 0.1486 | 0.0090 | 0.0488 |
| Week 24 | | | | |
| Original WOMAC pain subscale | | | | |
| N | 38 | 46 | 42 | 37 |
| Mean (SD) | 3.4 (2.15) | 3.6 (2.30) | 3.1 (2.31) | 3.1 (2.47) |
| Median | 3.4 | 3.3 | 2.7 | 2.4 |
| Min:Max | 0:8 | 0:8 | 0:9 | 0:8 |
| Change from baseline | | | | |
| N | 38 | 46 | 42 | 37 |
| Mean (SD) | −2.4 (2.19) | −2.0 (2.15) | −2.9 (2.46) | −2.8 (2.26) |
| Median | −2.0 | −1.8 | −2.5 | −3.0 |
| Min:Max | −8:1 | −7:2 | −8:3 | −9:2 |
| Difference vs. placebo [1] | | | | |
| LS Means (SE) | | −0.1 (0.45) | −0.7 (0.46) | −0.7 (0.47) |
| 95% CI | | −1.0:0.8 | −1.6:0.2 | −1.6:0.3 |
| P-value | | 0.8648 | 0.1513 | 0.1601 |

Note:
SD = standard deviation, CI = confidence interval, SE = standard error.
[1] The difference between each mAb1 treatment group and placebo in term of change from baseline.

As shown in Table 4, the baseline mean WOMAC Function Subscale scores were similar and ranged from 5.9 to 6.2. Treatment effect in terms of the LS mean differences vs. placebo for mAb1 0.03 mg/kg group was the smallest. For the two groups of patients given mAb1 at 0.1 mg/kg and 0.3 mg/kg, the treatment effects were similar and ranged from −0.6 to −1.6. The p-values were statistically significant for the week 8 duration and the week 16 duration, respectively, but not for the week 24 duration. For the group of patients given mAb1 at 0.03 mg/kg, the p-value was statistically significant for the week 8 duration and had a marginal value for the week 16 duration (p=0.0693), but was not significant for the week 24 duration.

TABLE 4

WOMAC Function Subscale from Baseline to Week 8, 16 and 24 --- Observed Data Using MMRM (Full Analysis Set)

| Week | Placebo (N = 55) | mAb1 (0.03 mg/kg) (N = 53) | mAb1 (0.1 mg/kg) (N = 53) | mAb1 (0.3 mg/kg) (N = 54) |
|---|---|---|---|---|
| Baseline | | | | |
| N | 55 | 52 | 53 | 54 |
| Mean (SD) | 5.9 (1.75) | 5.9 (1.83) | 6.2 (1.67) | 6.2 (2.07) |
| Median | 6.2 | 5.9 | 6.2 | 6.6 |
| Min:Max | 2:9 | 2:10 | 3:9 | 1:10 |
| Week 8 | | | | |
| Original WOMAC function subscale | | | | |
| N | 51 | 50 | 50 | 46 |
| Mean (SD) | 4.1 (2.08) | 3.1 (2.09) | 2.8 (2.14) | 2.6 (2.44) |
| Median | 4.5 | 2.6 | 2.4 | 1.5 |
| Min:Max | 0:8 | 0:10 | 0:7 | 0:8 |
| Change from baseline | | | | |
| N | 51 | 49 | 50 | 46 |
| Mean (SD) | −1.8 (1.95) | −2.8 (2.07) | −3.4 (2.32) | −3.4 (2.57) |
| Median | −1.4 | −3.1 | −3.2 | −3.5 |
| Min:Max | −7:2 | −7:2 | −9:1 | −9:5 |
| Difference vs. placebo [1] | | | | |
| LS Means (SE) | | −1.2 (0.41) | −1.6 (0.40) | −1.4 (0.40) |
| 95% CI | | −2.0:−0.4 | −2.4:−0.8 | −2.2:−0.6 |
| P-value | | 0.0037 | 0.0001 | 0.0005 |
| Week 16 | | | | |
| Original WOMAC function subscale | | | | |
| N | 44 | 47 | 44 | 41 |
| Mean (SD) | 3.6 (2.26) | 3.0 (2.21) | 2.7 (2.26) | 2.7 (2.43) |
| Median | 3.2 | 2.9 | 2.5 | 1.5 |
| Min:Max | 0:9 | 0:9 | 0:8 | 0:8 |
| Change from baseline | | | | |
| N | 44 | 47 | 44 | 41 |
| Mean (SD) | −2.3 (2.30) | −2.9 (1.78) | −3.4 (2.28) | −3.1 (2.18) |
| Median | −1.5 | −2.9 | −3.5 | −3.3 |
| Min:Max | −8:1 | −7:1 | −9:1 | −9:4 |
| Difference vs. placebo [1] | | | | |
| LS Means (SE) | | −0.8 (0.41) | −1.1 (0.41) | −0.9 (0.42) |
| 95% CI | | −1.6:0.1 | −1.9:−0.3 | −1.8:−0.1 |
| P-value | | 0.0693 | 0.0071 | 0.0245 |
| Week 24 | | | | |
| Original WOMAC function subscale | | | | |
| N | 38 | 46 | 42 | 37 |
| Mean (SD) | 3.4 (2.15) | 3.6 (2.35) | 3.2 (2.33) | 3.0 (2.43) |
| Median | 3.4 | 3.3 | 2.7 | 2.7 |
| Min:Max | 0:8 | 0:8 | 0:9 | 0:7 |
| Change from baseline | | | | |
| N | 38 | 46 | 42 | 37 |
| Mean (SD) | −2.4 (2.29) | −2.3 (2.05) | −2.9 (2.30) | −2.6 (2.40) |
| Median | −2.0 | −2.3 | −2.6 | −3.0 |
| Min:Max | −8:1 | −7:3 | −9:2 | −9:4 |
| Difference vs. placebo [1] | | | | |
| LS Means (SE) | | −0.3 (0.45) | −0.7 (0.45) | −0.6 (0.46) |
| 95% CI | | −1.2:0.6 | −1.5:0.2 | −1.5:0.3 |
| P-value | | 0.5214 | 0.1499 | 0.1748 |

Note:
SD = standard deviation, CI = confidence interval, SE = standard error.
[1] The difference between each mAb1 treatment group and placebo in term of change from baseline.

PGIC

The results of the patient-rated assessment of response to treatment (PGIC) are shown in Table 5.

TABLE 5

Patients Global Impression of Change (PGIC) at Week 8, 16 and 24--- Observed Data Using MMRM (Full Analysis Set)

| Week | Placebo (N = 55) | mAb1 (0.03 mg/kg) (N = 53) | mAb1 (0.1 mg/kg) (N = 53) | mAb1 (0.3 mg/kg) (N = 54) |
|---|---|---|---|---|
| Week 8 PGIC | | | | |
| N | 51 | 50 | 50 | 46 |
| Mean (SD) | 3.1 (1.21) | 2.3 (1.00) | 2.1 (1.10) | 2.1 (0.98) |
| Median | 3.0 | 2.0 | 2.0 | 2.0 |
| Min:Max | 1:6 | 1:4 | 1:5 | 1:4 |
| Difference vs. placebo [1] | | | | |
| LS Means (SE) | | −0.8 (0.21) | −1.0 (0.21) | −0.9 (0.21) |
| 95% CI | | −1.2:−0.4 | −1.4:−0.6 | −1.4:−0.5 |
| P-value | | 0.0002 | <0.0001 | <0.0001 |
| Week 16 PGIC | | | | |
| N | 44 | 47 | 43 | 41 |
| Mean (SD) | 2.8 (1.32) | 2.2 (0.95) | 2.5 (1.26) | 2.4 (1.16) |
| Median | 3.0 | 2.0 | 2.0 | 2.0 |
| Min:Max | 1:7 | 1:5 | 1:6 | 1:5 |
| Difference vs. placebo [1] | | | | |
| LS Means (SE) | | −0.7 (0.24) | −0.4 (0.24) | −0.5 (0.25) |
| 95% CI | | −1.1:−0.2 | −0.9:0.1 | −1.0:−0.1 |
| P-value | | 0.0056 | 0.1168 | 0.0297 |
| Week 24 PGIC | | | | |
| N | 38 | 46 | 42 | 37 |
| Mean (SD) | 2.7 (0.94) | 2.8 (1.41) | 2.7 (1.40) | 2.5 (1.07) |
| Median | 3.0 | 3.0 | 2.0 | 2.0 |
| Min:Max | 1:5 | 1:6 | 1:6 | 1:6 |
| Difference vs. placebo [1] | | | | |
| LS Means (SE) | | −0.1 (0.26) | −0.1 (0.27) | −0.3 (0.28) |
| 95% CI | | −0.6:0.5 | −0.6:0.5 | −0.8:0.2 |
| P-value | | 0.8274 | 0.8091 | 0.2710 |

Note:
SD = standard deviation, CI = confidence interval, SE = standard error.
[1] The difference between each mAb1 treatment group and placebo in term of change from baseline.

For all 3 mAb1 treatment groups at week 8, the LS means difference vs. placebo ranged from −1.0 to −0.8 and were statistically significant at the 5% level. Results of the patient groups given mAba1 at 0.03 mg/kg and 0.3 mg/kg as compared with placebo were statistically significant at week 16. None of the three mAb1 groups was significantly different from placebo at week 24.

Quality of Life Questionnaire (SF-12)

The results of the analyses from the Quality of Life questionnaire are shown in Table 6 (Physical Component Score) and Table 7 (Mental Component Score).

TABLE 6

SF-12 Physical Component Score (PCS) from Baseline to Week 8, 16 and 24 --- Observed Data Using MMRM (Full Analysis Set)

| Week | Placebo (N = 55) | mAb1 (0.03 mg/kg) (N = 53) | mAb1 (0.1 mg/kg) (N = 53) | mAb1 (0.3 mg/kg) (N = 54) |
|---|---|---|---|---|
| Baseline | | | | |
| N | 54 | 52 | 53 | 53 |
| Mean (SD) | 34.0 (8.06) | 32.0 (8.97) | 32.3 (9.65) | 33.6 (8.82) |
| Median | 31.9 | 32.6 | 30.7 | 33.2 |
| Min:Max | 19:53 | 14:57 | 9:55 | 16:53 |
| Week 8 | | | | |

TABLE 6-continued

SF-12 Physical Component Score (PCS) from Baseline to Week 8,
16 and 24 --- Observed Data Using MMRM (Full Analysis Set)

| Week | Placebo (N = 55) | mAb1 (0.03 mg/kg) (N = 53) | mAb1 (0.1 mg/kg) (N = 53) | mAb1 (0.3 mg/kg) (N = 54) |
|---|---|---|---|---|
| Original PCS | | | | |
| N | 51 | 50 | 49 | 46 |
| Mean (SD) | 37.4 (8.98) | 40.5 (9.24) | 41.5 (8.46) | 42.9 (8.43) |
| Median | 35.6 | 41.1 | 42.6 | 43.4 |
| Min:Max | 16:58 | 22:60 | 22:56 | 22:56 |
| Change from baseline | | | | |
| N | 50 | 49 | 49 | 45 |
| Mean (SD) | 2.9 (6.64) | 8.3 (8.18) | 9.0 (9.42) | 8.4 (9.29) |
| Median | 2.1 | 6.6 | 9.3 | 7.3 |
| Min:Max | −10:19 | −7:23 | −9:40 | −12:36 |
| Difference vs. placebo [1] | | | | |
| LS Means (SE) | | 4.4 (1.47) | 5.1 (1.46) | 5.6 (1.49) |
| 95% CI | | 1.5:7.3 | 2.2:8.0 | 2.6:8.5 |
| P-value | | 0.0034 | 0.0006 | 0.0002 |
| Week 16 Original PCS | | | | |
| N | 44 | 46 | 43 | 41 |
| Mean (SD) | 40.3 (8.82) | 41.7 (9.72) | 41.0 (9.31) | 43.2 (9.57) |
| Median | 39.5 | 40.3 | 40.5 | 42.2 |
| Min:Max | 24:59 | 22:62 | 21:63 | 26:61 |
| Change from baseline | | | | |
| N | 43 | 46 | 43 | 40 |
| Mean (SD) | 6.1 (8.43) | 9.7 (8.78) | 8.4 (10.57) | 9.2 (10.74) |
| Median | 5.7 | 8.3 | 8.1 | 8.0 |
| Min:Max | −11:23 | −6:30 | −8:42 | −8:38 |
| Difference vs. placebo [1] | | | | |
| LS Means (SE) | | 3.0 (1.72) | 1.9 (1.73) | 3.6 (1.76) |
| 95% CI | | −0.4:6.4 | −1.5:5.3 | 0.1:7.1 |
| P-value | | 0.0854 | 0.2647 | 0.0415 |
| Week 24 Original PCS | | | | |
| N | 38 | 46 | 42 | 37 |
| Mean (SD) | 40.3 (9.89) | 39.2 (10.39) | 40.2 (9.72) | 38.9 (9.45) |
| Median | 40.7 | 39.8 | 41.5 | 38.2 |
| Min:Max | 23:58 | 18:61 | 16:61 | 24:62 |
| Change from baseline | | | | |
| N | 37 | 46 | 42 | 36 |
| Mean (SD) | 6.6 (9.02) | 7.3 (10.09) | 7.2 (9.54) | 4.8 (10.52) |
| Median | 5.9 | 6.5 | 4.7 | 3.6 |
| Min:Max | −11:25 | −10:36 | −11:35 | −17:43 |
| Difference vs. placebo [1] | | | | |
| LS Means (SE) | | 1.2 (1.86) | 1.1 (1.89) | −0.6 (1.95) |
| 95% CI | | −2.5:4.8 | −2.6:4.9 | −4.4:3.3 |
| P-value | | 0.5340 | 0.5444 | 0.7759 |

Note:
SD = standard deviation, CI = confidence interval, SE = standard error.
[1] The difference between each mAb1 treatment group and placebo in term of change from baseline.

The baseline means SF-12 PCS were similar among the four groups. The LS mean vs. placebo at week 4 on PCS for the patient groups given mAb1 at 0.03 mg/kg, 0.1 mg/kg, and 0.3 mg/kg were 4.4, 5.1, and 5.6, respectively, with p-values of 0.0034, 0.0006, and 0.0002, respectively. The p-value was significant for the group given mAb1 at 0.3 mg/kg at week 16, but not for the other two groups. All p-values were non-significant at week 24.

TABLE 7

SF-12 Mental Component Score (MCS) from Baseline to Week 8,
16 and 24 --- Observed Data Using MMRM (Full Analysis Set)

| Week | Placebo (N = 55) | mAb1 (0.03 mg/kg) (N = 53) | mAb1 (0.1 mg/kg) (N = 53) | mAb1 (0.3 mg/kg) (N = 54) |
|---|---|---|---|---|
| Baseline | | | | |
| N | 54 | 52 | 53 | 53 |
| Mean (SD) | 51.7 (11.89) | 51.8 (11.73) | 51.4 (10.96) | 51.3 (11.63) |
| Median | 51.8 | 54.7 | 53.2 | 51.6 |
| Min:Max | 17:71 | 27:69 | 25:68 | 24:71 |
| Week 8 | | | | |
| Original MCS | | | | |
| N | 51 | 50 | 49 | 46 |
| Mean (SD) | 54.2 (9.43) | 54.2 (9.01) | 54.0 (8.55) | 53.7 (10.18) |
| Median | 56.6 | 55.4 | 56.5 | 55.1 |
| Min:Max | 30:69 | 33:70 | 31:67 | 25:69 |
| Change from baseline | | | | |
| N | 50 | 49 | 49 | 45 |
| Mean (SD) | 2.7 (9.70) | 1.9 (9.49) | 3.2 (9.06) | 1.8 (9.61) |
| Median | 0.9 | 0.9 | 1.6 | 1.1 |
| Min:Max | −19:33 | −19:21 | −11:37 | −20:25 |
| Difference vs. placebo [1] | | | | |
| LS Means (SE) | | −0.3 (1.50) | 0.3 (1.49) | −0.7 (1.53) |
| 95% CI | | −3.3:2.6 | −2.7:3.2 | −3.7:2.3 |
| P-value | | 0.8169 | 0.8557 | 0.6597 |
| Week 16 | | | | |
| Original MCS | | | | |
| N | 44 | 46 | 43 | 41 |
| Mean (SD) | 55.4 (8.16) | 52.5 (9.79) | 53.0 (9.17) | 52.2 (10.00) |
| Median | 57.4 | 54.7 | 54.2 | 53.7 |
| Min:Max | 34:67 | 25:68 | 22:67 | 27:71 |
| Change from baseline | | | | |
| N | 43 | 46 | 43 | 40 |
| Mean (SD) | 3.5 (11.28) | −0.4 (10.26) | 2.5 (7.66) | 0.2 (8.91) |
| Median | 1.3 | −0.2 | 1.4 | −0.2 |
| Min:Max | −19:33 | −38:28 | −12:16 | −13:17 |
| Difference vs. placebo [1] | | | | |
| LS Means (SE) | | −3.1 (1.57) | −1.8 (1.58) | −2.9 (1.61) |
| 95% CI | | −6.2:−0.0 | −4.9:1.3 | −6.1:0.3 |
| P-value | | 0.0488 | 0.2624 | 0.0749 |
| Week 24 | | | | |
| Original MCS | | | | |
| N | 38 | 46 | 42 | 37 |
| Mean (SD) | 53.5 (10.09) | 50.9 (9.97) | 54.9 (9.60) | 54.8 (9.07) |
| Median | 55.1 | 53.6 | 55.3 | 57.5 |
| Min:Max | 16:68 | 21:70 | 35:72 | 33:70 |
| Change from baseline | | | | |
| N | 37 | 46 | 42 | 36 |
| Mean (SD) | 1.4 (9.43) | −1.4 (10.35) | 4.5 (8.04) | 2.7 (10.69) |
| Median | 0.0 | −3.1 | 3.8 | 0.7 |
| Min:Max | −16:31 | −27:23 | −16:25 | −14:26 |
| Difference vs. placebo [1] | | | | |
| LS Means (SE) | | −2.9 (1.66) | 1.8 (1.68) | 1.1 (1.74) |
| 95% CI | | −6.2:0.3 | −1.5:5.1 | −2.3:4.5 |
| P-value | | 0.0775 | 0.2912 | 0.5316 |

Note:
SD = standard deviation, CI = confidence interval, SE = standard error.
[1] The difference between each mAb1 treatment group and placebo in term of change from baseline.

The baseline mean SF-12 Mental Component Score (MCS) was similar among the four groups. The p-values indicate non-significant results at all time points for all groups except for the group given mAb1 at 0.3 mg/kg at week 16 (p=0.0415).

Summary

The results of the key efficacy analysis showed that the 2 higher mAb1 doses (0.1 mg/kg and 0.3 mg/kg) consistently demonstrated significant treatment effects as compared with placebo up to week 16 on most efficacy endpoints.

What is claimed is:

1. A human antibody or antigen-binding fragment thereof that specifically binds human nerve growth factor (NGF), comprising:
   a) a heavy chain variable region (HCVR) of SEQ ID NO: 24; and
   b) a light chain variable region (LCVR) of SEQ ID NO: 26.

2. The antibody or antigen binding fragment of claim 1, characterized by a $K_D$ of about 5 pM or less, as measured by surface plasmon resonance; and
   wherein the antibody or antigen binding fragment thereof binds human NGF with an affinity of about 2-10-fold higher than the antibody or fragment binds rat and mouse NGF.

3. An injectable formulation, comprising:
   a pharmaceutically acceptable carrier, and
   a human antibody or antigen-binding fragment thereof that specifically binds human nerve growth factor (NGF), comprising:
   a) a heavy chain variable region (HCVR) of SEQ ID NO: 24; and
   b) a light chain variable region (LCVR) of SEQ ID NO: 26.

4. The injectable formulation of claim 3, wherein the human antibody or antigen-binding fragment thereof, specifically binds human nerve growth factor (NGF) with $K_D$ of 5 pM or less as measured by surface plasmon resonance; and
   wherein the antibody or fragment thereof binds human NGF with an affinity of about 2-10-fold higher than the antibody or fragment binds rat and mouse NGF.

5. The injectable formulation of claim 4, further comprising:
   a second therapeutic agent.

6. The injectable formulation of claim 5, wherein the second therapeutic agent is selected from the group consisting of an IL-1 and an IL-6 antagonist.

7. The injectable formulation of claim 4, further comprising:
   a polysorbate.

8. The injectable formulation of claim 4, further comprising:
   a polyethylene glycol.

9. The injectable formulation of claim 4, further comprising:
   a nonionic surfactant.

10. The injectable formulation of claim 4, further comprising:
    physiological saline.

11. The injectable formulation of claim 4, further comprising:
    a solubilizing agent.

12. A pre-filled device, comprising:
    a pharmaceutically acceptable carrier, and
    human antibody or antigen-binding fragment thereof that specifically binds human nerve growth factor (NGF), comprising:
    a) a heavy chain variable region (HCVR) of SEQ ID NO: 24; and
    b) a light chain variable region (LCVR) of SEQ ID NO: 26.

13. The pre-filled device of claim 12, wherein the device is a disposable pen delivery device prefilled with the carrier and human antibody or antigen-binding fragment thereof held in a reservoir within the device.

14. The pre-filled device of claim 12, wherein the human antibody or antigen-binding fragment thereof is present in a dose of 1 mg.

15. The pre-filled device of claim 12, wherein the device is a pre-filled syringe.

16. The prefilled device of claim 12, further comprising: a polysorbate.

17. A method of treating pain associated with a human nerve growth factor (NGF)-related condition or disease wherein the pain is inhibited, ameliorated, or reduced by inhibition of NGF, comprising:
    injecting a subject suffering from pain with an injectable formulation, comprising:
    a polysorbate;
    a diluent; and
    0.01 to 20 mg/kg body weight of the subject of a human antibody or antigen-binding fragment thereof that specifically binds human nerve growth factor (NGF), comprising:
    a) a heavy chain variable region (HCVR) of SEQ ID NO: 24; and
    b) a light chain variable region (LCVR) of SEQ ID NO:26.

18. The method of claim 17, wherein the pain associated with the NGF-related condition or disease is inhibited without significant impairment of motor coordination, and wherein human antibody or antigen-binding fragment thereof is injected in an amount of 0.02 to about 7 mg/kg body weight of the subject.

19. The method of claim 17, wherein the pain associated with the NGF-related condition or disease is inhibited without significant impairment of motor coordination, and wherein human antibody or antigen-binding fragment thereof is injected in an amount of 1 mg.

20. The method of claim 17, wherein the NGF-related condition or disease is selected from the group consisting of inflammatory pain, post-operative incision pain, neuropathic pain, fracture pain, gout joint pain, post-herpetic neuralgia, pain resulting from burns, cancer pain, osteoarthritis or rheumatoid arthritis pain, sciatica, and pains associated with sickle cell crises.

21. The method of claim 17, wherein the NGF-related condition is post-herpetic neuralgia.

22. The method of claim 17, further comprising administering a second therapeutic agent.

23. The method of claim 17, wherein the second therapeutic agent is an IL-1 or an IL-6 antagonist.

24. The method of claim 17, wherein the antibody or fragment thereof is administered by subcutaneous or intravenous administration.

25. The method of claim 24, wherein the pain associated with the NGF-related condition or disease is inhibited without significant impairment of motor coordination, and wherein human antibody or antigen-binding fragment thereof is injected in an amount of 1 mg.

26. The method according to claim 17, further comprising: administering a second therapeutic agent, wherein the second therapeutic agent is selected from the group consisting of an oral or injectable glucocorticoid, an opioid, tramadol, an alpha-2-delta ligand and hyaluronic acid.

27. The method of claim 17, wherein the antibody or antigen-binding fragment thereof is administered at a dose of 1 mg.

28. A method for treating osteoarthritis in a human subject in need thereof, comprising:
    administering to the subject a therapeutically effective amount of an anti-human nerve growth factor (NGF) antibody, or antigen-binding fragment thereof, wherein at least one symptom associated with osteoarthritis is prevented, ameliorated or improved, wherein the antibody or antigen-binding fragment comprises:
    a) a heavy chain variable region (HCVR) of SEQ ID NO: 24; and
    b) a light chain variable region (LCVR) of SEQ ID NO: 26.

* * * * *